(12) United States Patent
Kondo et al.

(10) Patent No.: US 9,073,868 B2
(45) Date of Patent: Jul. 7, 2015

(54) BENZAZEPINE DERIVATIVES USEFUL AS VASOPRESSIN ANTAGONISTS

(71) Applicant: Otsuka Pharmaceutical Co., Ltd., Tokyo (JP)

(72) Inventors: Kazumi Kondo, Osaka (JP); Yasuhiro Menjo, Osaka (JP); Takahiro Tomoyasu, Osaka (JP); Shin Miyamura, Osaka (JP); Yuso Tomohira, Osaka (JP); Takakuni Matsuda, Osaka (JP); Keigo Yamada, Osaka (JP); Yusuke Kato, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/034,979

(22) Filed: Sep. 24, 2013

(65) Prior Publication Data

US 2014/0024619 A1    Jan. 23, 2014

Related U.S. Application Data

(62) Division of application No. 12/666,751, filed as application No. PCT/JP2008/062033 on Jun. 26, 2008, now Pat. No. 8,669,229.

(30) Foreign Application Priority Data

Jun. 26, 2007   (JP) ................................. 2007-167207

(51) Int. Cl.
| | | |
|---|---|---|
| *A61K 38/00* | (2006.01) | |
| *C07D 223/16* | (2006.01) | |
| *C07D 405/12* | (2006.01) | |
| *C07F 9/553* | (2006.01) | |

(52) U.S. Cl.
CPC ............ *C07D 223/16* (2013.01); *C07D 405/12* (2013.01); *C07F 9/5535* (2013.01)

(58) Field of Classification Search
CPC .................................................... A61K 38/00
See application file for complete search history.

(56) References Cited

U.S. PATENT DOCUMENTS

| | | | |
|---|---|---|---|
| 5,045,478 A | 9/1991 | Wagner et al. | |
| 5,258,510 A | 11/1993 | Ogawa et al. | |
| 5,622,947 A | 4/1997 | Ogawa et al. | |
| 5,753,644 A | 5/1998 | Ogawa et al. | |
| 8,288,570 B2 | 10/2012 | Nelson et al. | |
| 2010/0004206 A1 | 1/2010 | Komatsu et al. | |

FOREIGN PATENT DOCUMENTS

| | | |
|---|---|---|
| CN | 1091288 A | 8/1994 |
| EP | 0602209 A1 | 6/1994 |
| EP | 1 042 296 B1 | 2/2004 |
| JP | 11-21241 | 1/1999 |
| JP | 2003-533504 A | 11/2003 |
| WO | WO94/01113 A1 | 1/1994 |
| WO | WO 00/18761 | 4/2000 |
| WO | WO 2006/050421 A1 | 5/2006 |

OTHER PUBLICATIONS

Mihai Gheorghiade, MD, "Vasopressin $V_2$-Receptor Blockage With Tolvaptan in Patients With Chronic Heart Failure," Circulation, 107, pp. 2690-2696 (2003).
Nagase, Hiroshi, Latest Innovation of Drug Chemistry (II), The Practice of Medicinal Chemistry; vol. 2, pp. 272-276 (1999).
International Search Report from the Japanese Patent Office for International Application No. PCT/JP2008/062033, mailed Oct. 22, 2008.
Jun Matsubara et al., "An Efficient Synthesis of Optical Isomers of Vasopressin $V_2$ Receptor Antagonist OPC-41061 by Lipase-Catalyzed Enantioselective Transesterification", Herocycles, vol. 54, No. 1, 2001, pp. 131-138.
Hiroshi Yamashita et al., "Practical Synthesis of Both Enantiomers of Vasopressin $V_2$ Receptor Antagonist OPC-41061 Using the Catalytic Asymmetric Hydrogenation", Heterocycles, vol. 56, 2002, pp. 123-128.
Povi Krogsgaard-Larsen et al., Textbook of Drug Design and Discovery, 2002, Chapter 14 (pp. 460-514).

*Primary Examiner* — James H Alstrum Acevedo
*Assistant Examiner* — Li Lee
(74) *Attorney, Agent, or Firm* — Finnegan, Henderson, Farabow, Garrett & Dunner, L.L.P.

(57) ABSTRACT

The present invention provides a benzazepine compound that can maintain for a long period of time the blood level of tolvaptan enabling to provide the desired pharmaceutical effects. The benzazepine compound of the present invention is represented by general formula (1)

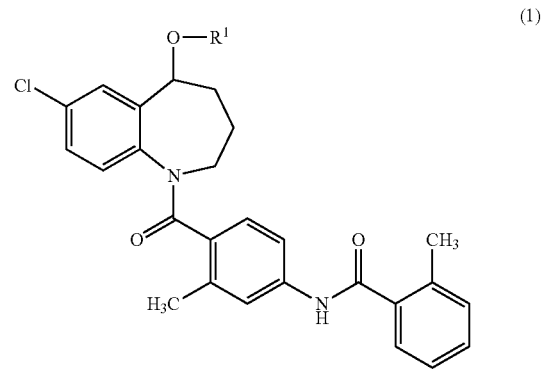

wherein $R^1$ represents a —CO—$(CH_2)_n$—$COR^2$ group (wherein n is an integer of 1 to 4, and $R^2$ is (2-1) a hydroxy group; (2-2) a lower alkoxy group optionally substituted with a hydroxy group, a lower alkanoyl group, a lower alkanoyloxy group, a lower alkoxycarbonyloxy group, a cycloalkyloxycarbonyloxy group, or 5-methyl-2-oxo-1,3-dioxol-4-yl; or (2-3) an amino group optionally substituted with a hydroxy-lower alkyl group), or the like.

4 Claims, No Drawings

BENZAZEPINE DERIVATIVES USEFUL AS VASOPRESSIN ANTAGONISTS

This is a division of Application No. 12/666,751, §371 date of Nov. 18, 2010, which is the National Stage Application of PCT/JP2008/062033, filed Jun. 26, 2008, and claims priority to JP 2007-167207 filed Jun. 26, 2007, all of which are incorporated herein by reference.

TECHNICAL FIELD

The present invention relates to a novel benzazepine compound and a pharmaceutical preparation.

BACKGROUND ART

Tolvaptan represented by the following formula (2) is a known compound, and is disclosed, for example, in U.S. Pat. No. 5,258,510 (Example 1199).

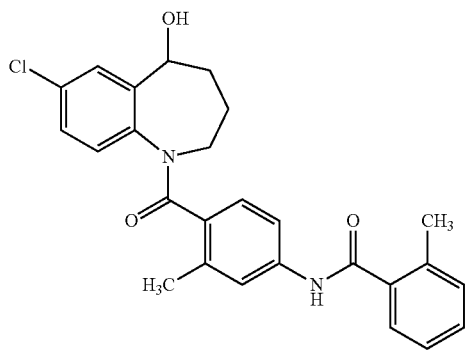

(2)

Tolvaptan is known to be useful as a vasopressin antagonist having aquaretic efficacy (Circulation, 107, pp. 2690-2696 (2003)). However, because of its low water solubility, tolvaptan has problems in that it is poorly absorbed from the gastrointestinal tract, and its dosage form and administration route are limited. From the viewpoint of medical treatment, the development of a new drug that can maintain for a long period of time the blood level of tolvaptan enabling to provide the desired pharmaceutical effects has been desired.

DISCLOSURE OF THE INVENTION

An object of the present invention is to provide a novel benzazepine compound that has excellent properties, such as the maintenance of the blood level of tolvaptan for a long period of time enabling to provide the desired pharmaceutical effects.

The present inventors carried out extensive research to overcome the above problem, and as a result found that benzazepine compounds represented by general formula (1) have excellent properties, such as the maintenance of pharmaceutical effects of the active ingredient tolvaptan for a long period of time in the body. The present invention has been accomplished based on the above findings.

The present invention provides the following benzazepine compounds, and pharmaceutical preparations containing the compounds shown in Items 1 to 3 below.

Item 1. A benzazepine compound represented by general formula (1)

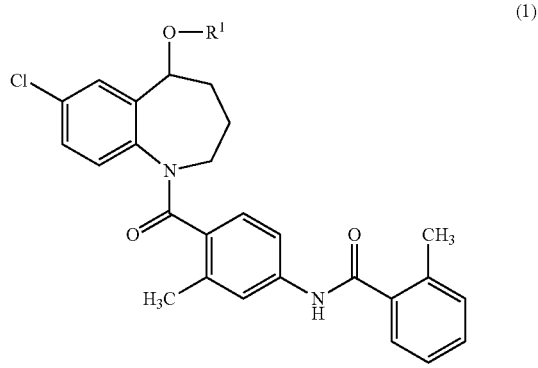

(1)

wherein $R^1$ is a group of (1-1) to (1-7):

(1-1) a —CO—$(CH_2)_n$—$COR^2$ group wherein n is an integer of 1 to 4, $R^2$ is (2-1) a hydroxy group; (2-2) a lower alkoxy group optionally substituted with a hydroxy group, a lower alkanoyl group, a lower alkanoyloxy group, a lower alkoxycarbonyloxy group, a cycloalkyloxycarbonyloxy group, or 5-methyl-2-oxo-1,3-dioxol-4-yl; or (2-3) an amino group optionally substituted with a hydroxy-lower alkyl group;

(1-2) a —CO—$(CH_2)_m$—$NR^3R^4$ group wherein m is an integer of 0 to 4, $R^3$ is a hydrogen atom or a lower alkyl group, $R^4$ is (4-1) a hydrogen atom; (4-2) a lower alkyl group optionally substituted with a halogen atom, a lower alkylamino group, a lower alkoxycarbonyl group, or 5-methyl-2-oxo-1,3-dioxol-4-yl; or (4-3) a lower alkoxycarbonyl group optionally substituted with a halogen atom, a lower alkanoyloxy group, or 5-methyl-2-oxo-1,3-dioxol-4-yl, $R^3$ and $R^4$ may form a 5- to 6-membered saturated heterocyclic ring by bonding $R^3$ and $R^4$ to each other, together with the nitrogen atom to which $R^3$ and $R^4$ bond, directly or via a nitrogen atom or oxygen atom, the heterocyclic ring being optionally substituted with (4-4) a lower alkyl group optionally substituted with a hydroxy-lower alkoxy group; (4-5) a lower alkoxycarbonyl group; (4-6) an alkylcarbonyl group (optionally substituted on the alkyl group with a carboxyl group or a lower alkoxycarbonyl group); (4-7) an arylcarbonyl group; or (4-8) a furylcarbonyl group;

(1-3) a —CO—$(CH_2)_p$—O—CO—$NR^5R^6$ group wherein p is an integer of 1 to 4, $R^5$ is a lower alkyl group, and $R^6$ is a lower alkoxycarbonyl-lower alkyl group;

(1-4) a —CO—$(CH_2)_q$—X—$R^7$ group wherein q is an integer of 1 to 4, X is an oxygen atom, a sulfur atom, or a sulfonyl group, and $R^7$ is a carboxy-lower alkyl group, or a lower alkoxycarbonyl lower alkyl group;

(1-5) a —CO—$R^8$ group (wherein $R^8$ is (8-1) an alkyl group optionally substituted with a halogen atom, a lower alkanoyloxy group, or a phenyl group (substituted with a dihydroxy phosphoryloxy group in which the hydroxy groups are optionally substituted with benzyl groups, and a lower alkyl group), (8-2) a lower alkoxy group substituted with a halogen atom, a lower alkanoyloxy group, or a dihydroxyphosphoryloxy group, (8-3) a pyridyl group, or (8-4) a lower alkoxyphenyl group;

(1-6) a lower alkyl group substituted with a group selected from the group consisting of lower alkylthio groups, a dihydroxyphosphoryloxy group, and lower alkanoyloxy groups; and (1-7) an amino acid or peptide residue optionally protected with one or more protecting groups; or a salt thereof.

Item 2. The compound according to Item 1, wherein, in formula (1), $R^1$ is a group selected from the group consisting of: —CO—$(CH_2)_n$—COOH, wherein n is an integer of 1 to 4; —CO—$R^8$, wherein $R^8$ is an alkyl group; and, an amino acid or peptide residue optionally protected with one or more protecting groups; or a salt thereof.

Item 3. The compound according to Item 1, wherein, in formula (1), $R^1$ is alanyl, sarcosyl, N-ethylglycyl, N-propylglycyl, N-methyl-N-ethylglycyl, N-methyl-N-propylglycyl, N-methyl-N-butylglycyl, N-methyl-N-pentylglycyl, or N-methyl-N-hexylglycyl; or a peptide residue selected from the group consisting of: sarcosyl-glycyl, glycyl-glycyl, glycyl-sarcosyl, glycyl-alanyl, alanyl-glycyl, sarcosyl-sarcocyl, glycyl-phenylalanyl, phenylalanyl-glycyl, phenylalanyl-phenylalanyl, glycyl-glycyl-glycyl, N,N-dimethylglycyl-glycyl, N-methyl-N-ethylglycyl-glycyl, sarcosyl-glycyl-glycyl, and N,N-dimethylglycyl-glycyl-glycyl, each of which is optionally protected with one or more protecting groups; or a salt thereof.

Item 4. The compound according to Item 3, wherein, in formula (1), $R^1$ is a peptide residues selected from the group consisting of: sarcosyl-glycyl, glycyl-glycyl, glycyl-sarcosyl, glycyl-alanyl, alanyl-glycyl, glycyl-phenylalanyl, phenylalanyl-glycyl, phenylalanyl-phenylalanyl, glycyl-glycyl-glycyl, N,N-dimethylglycyl-glycyl, N-methyl-N-ethylglycyl-glycyl, and N,N-dimethylglycyl-glycyl-glycyl, each of which is optionally protected with one or more protecting groups; or a salt thereof.

Item 5. A pharmaceutical preparation comprising the benzazepine compound of Item 1 or a pharmacologically acceptable salt thereof, and a pharmacologically acceptable diluent and/or carrier.

Item 6. The pharmaceutical preparation according to Item 5 which is used as a vasodilator, hypotensive drug, aquaretic agent, or platelet aggregation inhibitor.

Specific examples of the groups in general formula (1) are as follows.

In this specification, the term "lower" refers to "$C_{1-6}$", unless otherwise specified.

Examples of lower alkanoyl groups include straight or branched $C_{2-6}$ alkanoyl groups, such as acetyl, n-propionyl, n-butyryl, isobutyryl, n-pentanoyl, tert-butyl carbonyl, and n-hexanoyl.

Examples of lower alkanoyloxy groups include straight or branched $C_{2-6}$ alkanoyloxy groups, such as acetyloxy, n-propionyloxy, n-butyryloxy, isobutyryloxy, n-pentanoyloxy, tert-butylcarbonyloxy, and n-hexanoyloxy group.

Examples of lower alkoxycarbonyloxy groups include alkoxycarbonyloxy groups in which the alkoxy moiety is a straight or branched $C_{1-6}$ alkoxy group, such as methoxycarbonyloxy, ethoxycarbonyloxy, n-propoxycarbonyloxy, isopropoxycarbonyloxy, n-buthoxycarbonyloxy, isobuthoxycarbonyloxy, tert-buthoxycarbonyloxy, sec-buthoxycarbonyloxy, n-pentyloxycarbonyloxy, neopentyloxycarbonyloxy, n-hexyloxycarbonyloxy, isohexyloxycarbonyloxy, and 3-methyl pentyloxycarbonyloxy.

Examples of cycloalkyloxycarbonyloxy groups include cycloalkyloxycarbonyloxy groups in which the cycloalkyl moiety is a $C_{3-8}$ cycloalkyl group, such as cyclopropyloxycarbonyloxy, cyclobutyloxycarbonyloxy, cyclopentyloxycarbonyloxy, cyclohexyloxycarbonyloxy, cycloheptyloxycarbonyloxy, and cyclooctyloxycarbonyloxy.

Examples of cycloalkylcarbonyl groups include cycloalkylcarbonyl groups in which the cycloalkyl moiety is a $C_{3-8}$ cycloalkyl group, such as cyclopropylcarbonyl, cyclobutylcarbonyl, cyclopentylcarbonyl, cyclohexylcarbonyl, cycloheptylcarbonyl, and cyclooctylcarbonyl.

Examples of lower alkoxy groups include straight or branched $C_{1-6}$ alkoxy groups, such as methoxy, ethoxy, n-propoxy, isopropoxy, n-butoxy, isobutoxy, tert-butoxy, sec-butoxy, n-pentyloxy, isopentyloxy, neopentyloxy, n-hexyloxy, isohexyloxy, and 3-methylpentyloxy.

Examples of hydroxy-lower alkyl groups include straight or branched $C_{1-6}$ alkyl groups having one to three hydroxy groups, such as hydroxymethyl, 2-hydroxyethyl, 1-hydroxyethyl, 3-hydroxypropyl, 2,3-dihydroxypropyl, 4-hydroxybutyl, 3,4-dihydroxybutyl, 1,1-dimethyl-2-hydroxyethyl, 5-hydroxypentyl, 6-hydroxyhexyl, 3,3-dimethyl-3-hydroxypropyl, 2-methyl-3-hydroxypropyl, and 2,3,4-trihydroxybutyl.

Examples of lower alkyl groups include straight or branched $C_{1-6}$ alkyl groups, such as methyl, ethyl, n-propyl, isopropyl, n-butyl, isobutyl, tert-butyl, sec-butyl, n-pentyl, isopentyl, neopentyl, n-hexyl, isohexyl, and 3-methylpentyl.

Examples of halogen atoms include fluorine, chlorine, bromine, and iodine.

Examples of lower alkylamino groups include amino groups substituted with one to two straight or branched $C_{1-6}$ alkyl groups, such as methylamino, ethylamino, n-propylamino, isopropylamino, n-butylamino, tert-butylamino, n-pentylamino, n-hexylamino, dimethylamino, diethylamino, di-n-propylamino, di-n-butylamino, di-n-pentylamino, di-n-hexylamino, N-methyl-N-ethylamino, N-ethyl-N-n-propylamino, N-methyl-N-n-butylamino, and N-methyl-N-n-hexylamino.

Examples of lower alkoxycarbonyl groups include alkoxycarbonyl groups in which the alkoxy moiety is a straight or branched $C_{1-6}$ alkoxy group, such as methoxycarbonyl, ethoxycarbonyl, n-propoxycarbonyl, isopropoxycarbonyl, n-butoxycarbonyl, isobutoxycarbonyl, tert-butoxycarbonyl, sec-butoxycarbonyl, n-pentyloxycarbonyl, neopentyloxycarbonyl, n-hexyloxycarbonyl, isohexyloxycarbonyl, and 3-methylpentyloxycarbonyl.

Examples of 6-membered saturated heterocyclic rings formed by bonding $R^3$ and $R^4$ to each other, together with the nitrogen atom to which $R^3$ and $R^4$ bond, directly or via a nitrogen atom or oxygen atom include piperazine, piperidine, morpholine, and the like.

Examples of hydroxy-lower alkoxy groups include hydroxyalkoxy groups that have one or two hydroxy groups, the alkoxy moiety being a straight or branched $C_{1-6}$ alkoxy group, such as hydroxymethoxy, 2-hydroxyethoxy, 1-hydroxyethoxy, 3-hydroxypropoxy, 4-hydroxybutoxy, 5-hydroxypentyloxy, 6-hydroxyhexyloxy, 1,1-dimethyl-2-hydroxyethoxy, and 2-methyl-3-hydroxypropoxy.

Examples of alkylcarbonyl groups include alkylcarbonyl groups in which the alkyl moiety is a straight or branched $C_{1-20}$ alkyl group, such as methylcarbonyl, ethylcarbonyl, n-propylcarbonyl, isopropylcarbonyl, n-butylcarbonyl, isobutylcarbonyl, tert-butylcarbonyl, sec-butylcarbonyl, n-pentylcarbonyl, isopentylcarbonyl, neopentylcarbonyl, n-hexylcarbonyl, isohexylcarbonyl, 3-methylpentylcarbonyl, n-heptylcarbonyl, n-octylcarbonyl, n-nonylcarbonyl, n-decylcarbonyl, n-undecylcarbonyl, n-dodecylcarbonyl, n-tridecylcarbonyl, n-tetradecylcarbonyl, n-pentadecylcarbonyl, n-hexadecylcarbonyl, n-heptadecylcarbonyl, n-octadecylcarbonyl, n-nonadecylcarbonyl, and n-icosylcarbonyl.

Examples of arylcarbonyl groups include phenylcarbonyl, (1- or 2-)naphthylcarbonyl, and the like.

Examples of furylcarbonyl groups include (2- or 3-)furylcarbonyl.

Examples of lower alkoxycarbonyl lower alkyl groups include alkoxycarbonylalkyl groups in which the alkoxy moiety is a straight or branched $C_{1-6}$ alkoxy group, and the alkyl moiety is a straight or branched $C_{1-6}$ alkyl group, such as methoxycarbonylmethyl, ethoxycarbonylmethyl, 2-methoxycarbonylethyl, 2-ethoxycarbonylethyl, 1-ethoxycarbonylethyl, 3-methoxycarbonylpropyl, 3-ethoxycarbonylpropyl, 4-ethoxycarbonylbutyl, 5-isopropoxycarbonyl pentyl, 6-n-propoxycarbonylhexyl, 1,1-dimethyl-2-n-butoxycarbonylethyl, 2-methyl-3-tert-butoxycarbonylpropyl, 2-n-pentyloxycarbonylethyl, and n-hexyloxycarbonylmethyl.

Examples of carboxy lower alkyl groups include carboxy alkyl groups in which the alkyl moiety is a straight or branched $C_{1-6}$ alkyl group, such as carboxymethyl, 2-carboxyethyl, 1-carboxyethyl, 3-carboxypropyl, 4-carboxybutyl, 5-carboxypentyl, 6-carboxyhexyl, 1,1-dimethyl-2-carboxyethyl, and 2-methyl-3-carboxypropyl.

Examples of lower alkoxy phenyl groups include alkoxyphenyl groups in which the alkoxy moiety is a straight or branched $C_{1-6}$ alkoxy group, such as methoxyphenyl, ethoxyphenyl, n-propoxyphenyl, isopropoxyphenyl, n-butoxyphenyl, isobutoxyphenyl, tert-butoxyphenyl, sec-butoxyphenyl, n-pentyloxyphenyl, isopentyloxyphenyl, neopentyloxyphenyl, n-hexyloxyphenyl, isohexyloxyphenyl, and 3-methylpentyloxyphenyl.

Examples of lower alkylthio groups include a straight or branched $C_{1-6}$ alkylthio groups, such as methylthio, ethylthio, n-propylthio, isopropylthio, n-butylthio, tert-butylthio, n-pentylthio, and n-hexylthio.

Examples of amino acid or peptide residues include amino acid residues such as alanyl, phenylalanyl, sarcosyl, valyl, leucyl, isoleucyl, prolyl, N-ethylglycyl, N-propylglycyl, N-isopropylglycyl, N-butylglycyl, N-tert-butylglycyl, N-pentylglycyl, N-hexylglycyl, N,N-diethylglycyl, N,N-dipropylglycyl, N,N-dibutylglycyl, N,N-dipentylglycyl, N,N-dihexylglycyl, N-methyl-N-ethylglycyl, N-methyl-N-propylglycyl, N-methyl-N-butylglycyl, N-methyl-N-pentylglycyl, and N-methyl-N-hexylglycyl; and peptide residues such as sarcosyl-glycyl, glycyl-glycyl, glycyl-sarcosyl, sarcosyl-sarcosyl, alanyl-glycyl, phenylalanyl-glycyl, phenylalanyl-phenylalanyl, glycyl-glycyl-glycyl, N-ethylglycyl-glycyl, N-propylglycyl-glycyl, N,N-dimethylglycyl-glycyl, N,N-diethylglycyl-glycyl, N-methyl-N-ethylglycyl-glycyl, sarcosyl-glycyl-glycyl, N-ethylglycyl-glycyl-glycyl, and N,N-dimethylglycyl-glycyl-glycyl.

Examples of protecting groups for amino acids and peptides include those usually used to protect amino groups of amino acids or peptides, such as tert-butoxycarbonyl, benzyloxycarbonyl, fluorenylmethoxycarbonyl, and acetyl.

The benzazepine compounds represented by general formula (1) can be prepared by various methods; for example, by the processes according to the following Reaction Schemes.

Among the benzazepine compounds represented by general formula (1) or salts thereof, Compound (1a) wherein $R^1$ is a group of (1-1) to (1-5) or (1-7) above can be prepared from tolvaptan of formula (2) according to Reaction Scheme-1, 2, or 3.

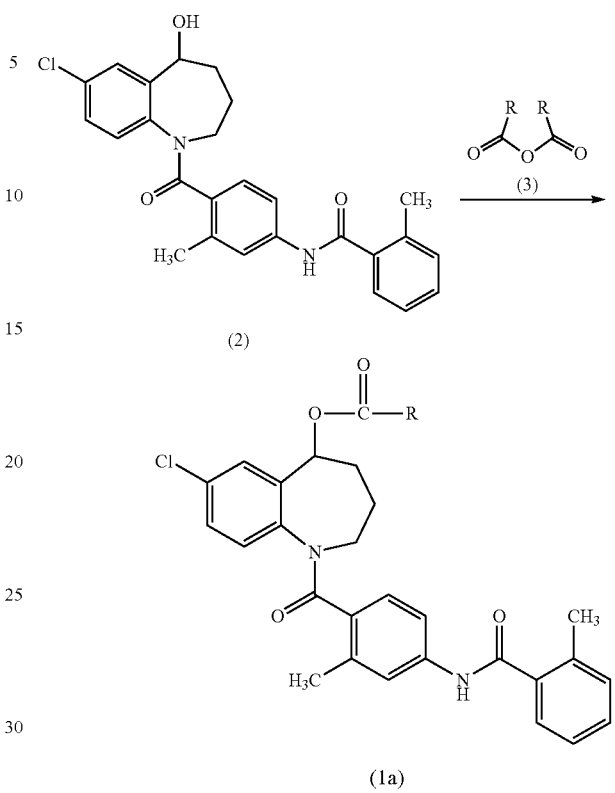

Reaction Scheme-1

(2)

(1a)

wherein R is —$(CH_2)_n$—$COR^2$ (wherein n and $R^2$ are as defined above), —$(CH_2)_m$—$NR^3R^4$ (wherein m, $R^3$ and $R^4$ are as defined above), —$(CH_2)_p$—O—CO—$NR^5R^6$ (wherein p, $R^5$ and $R^6$ are as defined above), —$(CH_2)_q$—X—$R^7$ (wherein q, X, and $R^7$ are as defined above), —$R^8$ (wherein $R^8$ is as defined above), or a group formed by removing a carbonyl group (CO group) from an amino acid or peptide residue optionally protected with one or more protecting groups (e.g., aminomethyl for glycyl, (R)-1-aminoethyl for alanyl, (R)-1-amino-2-phenylpropyl for phenylalanyl, (methylamino)methyl for sarcosyl, (R)-1-amino-3-methylbutyl for leucyl, tert-butoxycarbonyl(ethyl)aminomethyl for N-tert-butoxycarbonyl-N-ethylglycyl, (S)-2-aminopropanamidomethyl for alanyl-glycyl, 2-(methylamino)acetamido-methyl for sarcosyl-glycyl, (S)-2-amino-3-phenylpropanamidomethyl for phenylalanyl-glycyl, (2-aminoacetamido)acetamidomethyl for glycyl-glycyl-glycyl, [2-(methylamino)acetamido]acetamidomethyl for sarcosyl-glycyl-glycyl, or the like.).

According to the process shown in Reaction Scheme-1, Compound (1a) is prepared by reacting Compound (2) with an acid anhydride (3) in the presence or absence of a basic compound in a suitable solvent.

The amount of acid anhydride (3) is usually about 1 mole to a large excess, and preferably about 1 to about 10 moles, per mole of Compound (2).

The solvent may be any known solvent that does not adversely affect the reaction. Examples of such solvents include ethers such as diethyl ether, dioxane, tetrahydrofuran, monoglyme, and diglyme; halogenated hydrocarbons such as methylene chloride, chloroform, 1,2-dichloroethane, and carbon tetrachloride; esters such as ethyl acetate; aromatic hydrocarbons such as benzene, toluene, and xylene; aprotic polar solvents such as acetonitrile, dimethylformamide (DMF), dimethyl sulfoxide (DMSO), and N-methylpyrrolidone (NMP); and mixed solvents thereof.

Examples of basic compounds include triethylamine, pyridine, and the like. The amount of basic compound is usually at least about 1 mole, and preferably about 1 to about 10 moles, per mole of Compound (2). Such a basic compound can also be used as the solvent.

When a catalyst such as 4-dimethylaminopyridine is present in the reaction system in the above reaction, the reaction can be promoted.

The reaction temperature of the above reaction is usually room temperature to 150° C., and preferably room temperature to 100° C. The reaction time is usually 15 minutes to 24 hours, preferably 30 minutes to 6 hours, and more preferably 1 to 3 hours.

Examples of basic compounds include carbonates such as sodium carbonate, potassium carbonate, sodium hydrogen carbonate, potassium hydrogen carbonate, and cesium carbonate; phosphates such as potassium phosphate, and sodium phosphate; organic bases such as pyridine, imidazole, N-ethyldiisopropylamine, dimethylaminopyridine, triethylamine, trimethylamine, dimethylaniline, N-methylmorpholine, 1,5-diazabicyclo[4.3.0]nonene-5 (DBN), 1,8-diazabicyclo[5.4.0]undecene-7 (DBU), and 1,4-diazabicyclo[2.2.2]octane (DABCO); and mixtures thereof.

The amount of basic compound is usually at least about 1 mole, and preferably about 1 to about 10 moles, per mole of Compound (2). Such an organic base can also be used as the solvent.

When a catalyst such as 4-dimethylaminopyridine is present in the reaction system in the above reaction, the reaction can be promoted.

The reaction temperature of the above reaction is usually −10° C. to 100° C., and preferably 0° C. to 50° C., and more preferably 0° C. to room temperature. The reaction time is usually 15 minutes to 24 hours, preferably 30 minutes to 6 hours, and more preferably 1 to 3 hours.

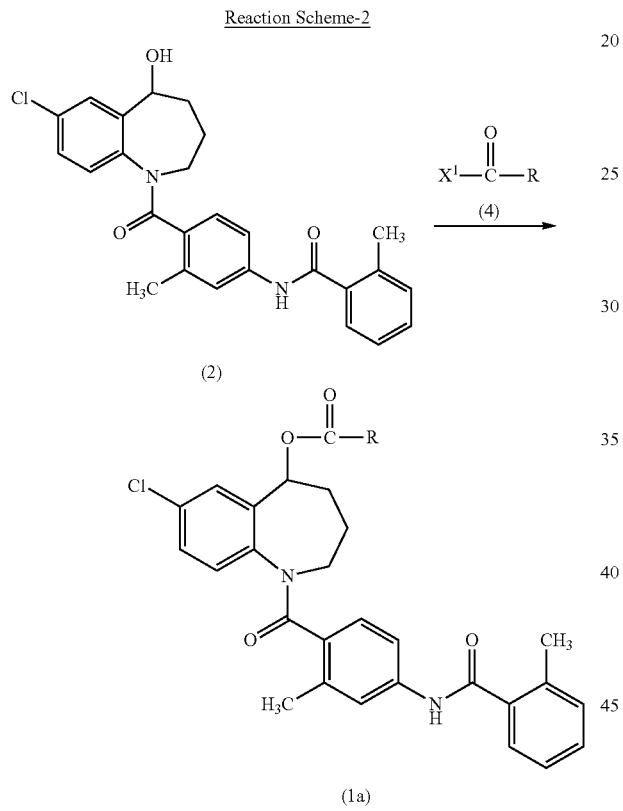

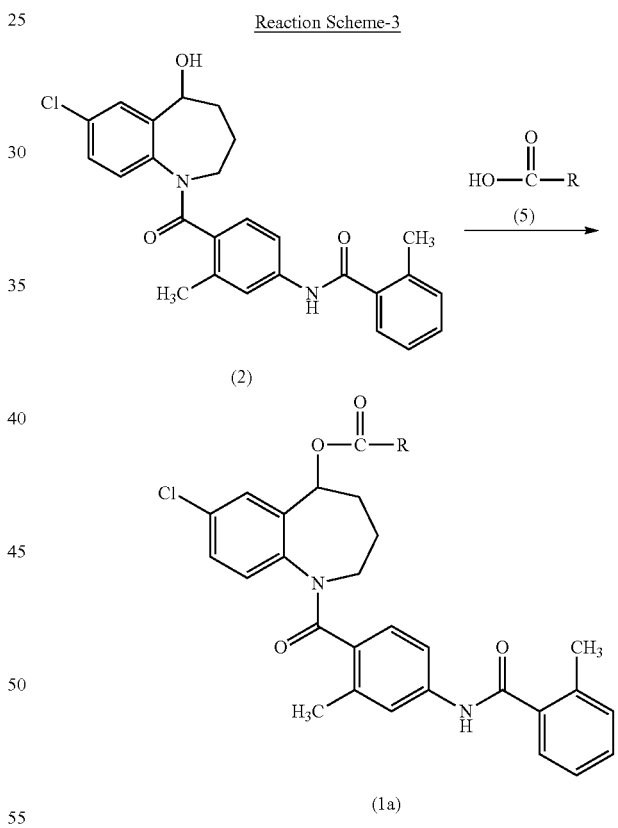

wherein R is as defined above, and $X^1$ is a halogen atom.

According to the process shown in Reaction Scheme-2, Compound (2) is reacted with an acid halide (4) in the presence of a basic compound in a suitable solvent to prepare Compound (1a).

The amount of acid halide (4) is usually about 1 mole to a large excess, and preferably about 1 to about 10 moles, per mole of Compound (2).

The solvent may be any known solvent that does not adversely affect the reaction. Examples of such solvents include ethers such as diethyl ether, dioxane, tetrahydrofuran, monoglyme, and diglyme; halogenated hydrocarbons such as methylene chloride, chloroform, 1,2-dichloroethane, and carbon tetrachloride; esters such as ethyl acetate; aromatic hydrocarbons such as benzene, toluene, and xylene; aprotic polar solvents such as acetonitrile, DMF, DMSO, and NMP; and mixed solvents thereof.

wherein R is as defined above.

According to the process shown in Reaction Scheme-3, Compound (2) is condensed with a carboxylic acid (5) in the presence of an activator to prepare Compound (1a).

The amount of carboxylic acid (5) is usually about 1 to about 10 moles, and preferably about 1 to about 5 moles, per mole of Compound (2).

Examples of activators include dicyclohexylcarbodiimide, 1-(3-dimethylaminopropyl)-3-ethylcarbodiimide (WSC), carbonyldiimidazole, and the like. Such activators can be used singly or in a combination of two or more.

The amount of activator is usually at least about 1 mole, and preferably about 1 mole to about 5 moles, per mole of Compound (2).

The condensation reaction is usually carried out in a suitable solvent in the presence or absence of a basic compound. Examples of solvents that can be used include ethers such as diethyl ether, dioxane, tetrahydrofuran, monoglyme, and diglyme; halogenated hydrocarbons such as methylene chloride, chloroform, 1,2-dichloroethane, and carbon tetrachloride; esters such as ethyl acetate; aromatic hydrocarbons such as benzene, toluene, and xylene; aprotic polar solvents such as acetonitrile, DMF, DMSO, and NMP; and mixed solvents thereof.

Examples of basic compounds include triethylamine, pyridine, and the like. The amount of basic compound is usually at least about 1 mole, and preferably about 1 to about 10 moles, per mole of Compound (2). Such a basic compound can also be used as the solvent.

When a catalyst such as 4-dimethylaminopyridine is present in the reaction system, the reaction can be promoted.

The reaction is usually carried out at about −20° C. to about 100° C., and preferably at 0° C. to room temperature. The reaction usually completes in about 5 minutes to about 90 hours.

Among the benzazepine compounds represented by general formula (1) or salts thereof, Compound (1b) wherein $R^1$ is a group of (1-6) above (a lower alkyl group substituted with a lower alkylthio group) can be prepared from tolvaptan of formula (2) by the process according to the following Reaction Scheme-4:

The process shown in Reaction Scheme-4 is a reaction to convert the hydrogen atom of the hydroxy group of Compound (2) into a lower alkyl group substituted with a lower alkylthio group. For example, to convert the hydrogen atom of the hydroxy group of Compound (2) into a methylthiomethyl group, Compound (2) is subjected to the common ether-bond-formation reaction, so-called Pummerer reaction, or the like. The common ether-bond-formation reaction is usually carried out in a conventional solvent that does not affect the reaction, and the reaction temperature is not critical. The Pummerer reaction is as shown in Reaction Scheme-4-1 below; the compound (2) is reacted with sulfoxide (6), such as dimethyl sulfoxide, in the presence of acetic anhydride and acetic acid at room temperature to about 70° C. for about 4 to about 72 hours.

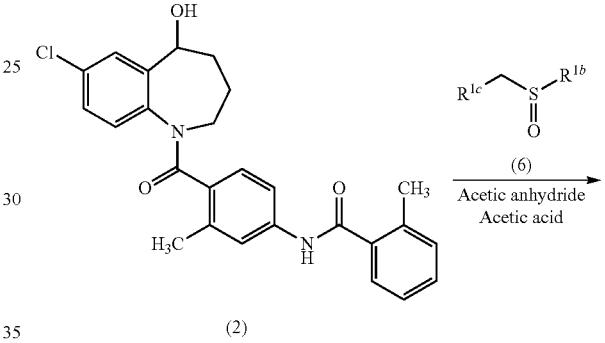

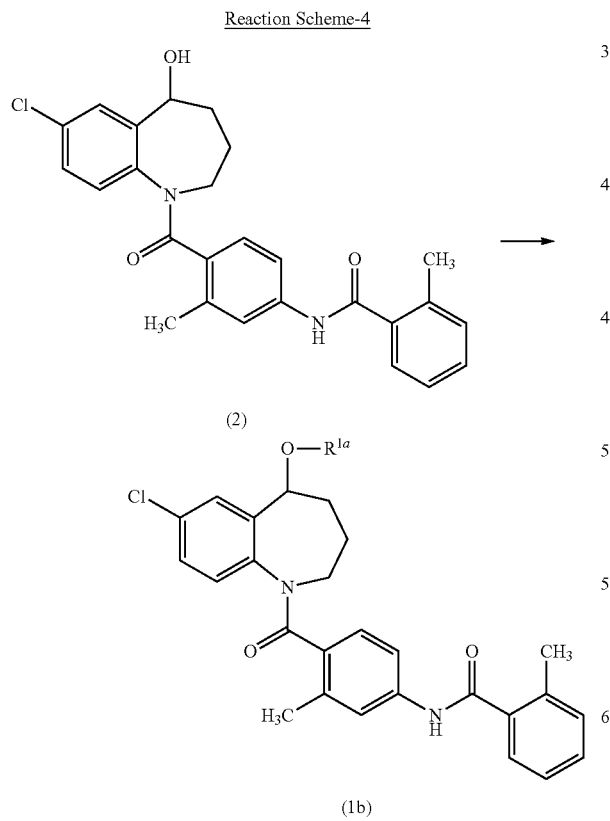

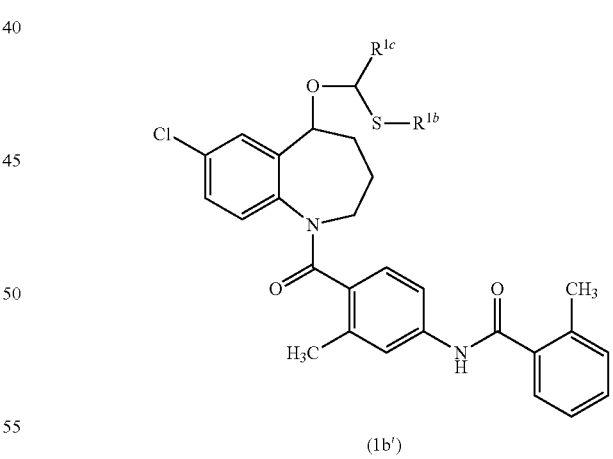

wherein $R^{1a}$ is a lower alkyl group substituted with a lower alkylthio group.

wherein $R^{1b}$ and $R^{1c}$ are independently a lower alkyl group.

Among the benzazepine compounds represented by general formula (1) or salts thereof, Compound (1c) wherein $R^1$ is a group of (1-6) above (a lower alkyl group substituted with a dihydroxyphosphoryloxy group) can be prepared, for example, from Compound (1b) by the process according to the following Reaction Scheme-5:

Reaction Scheme-5

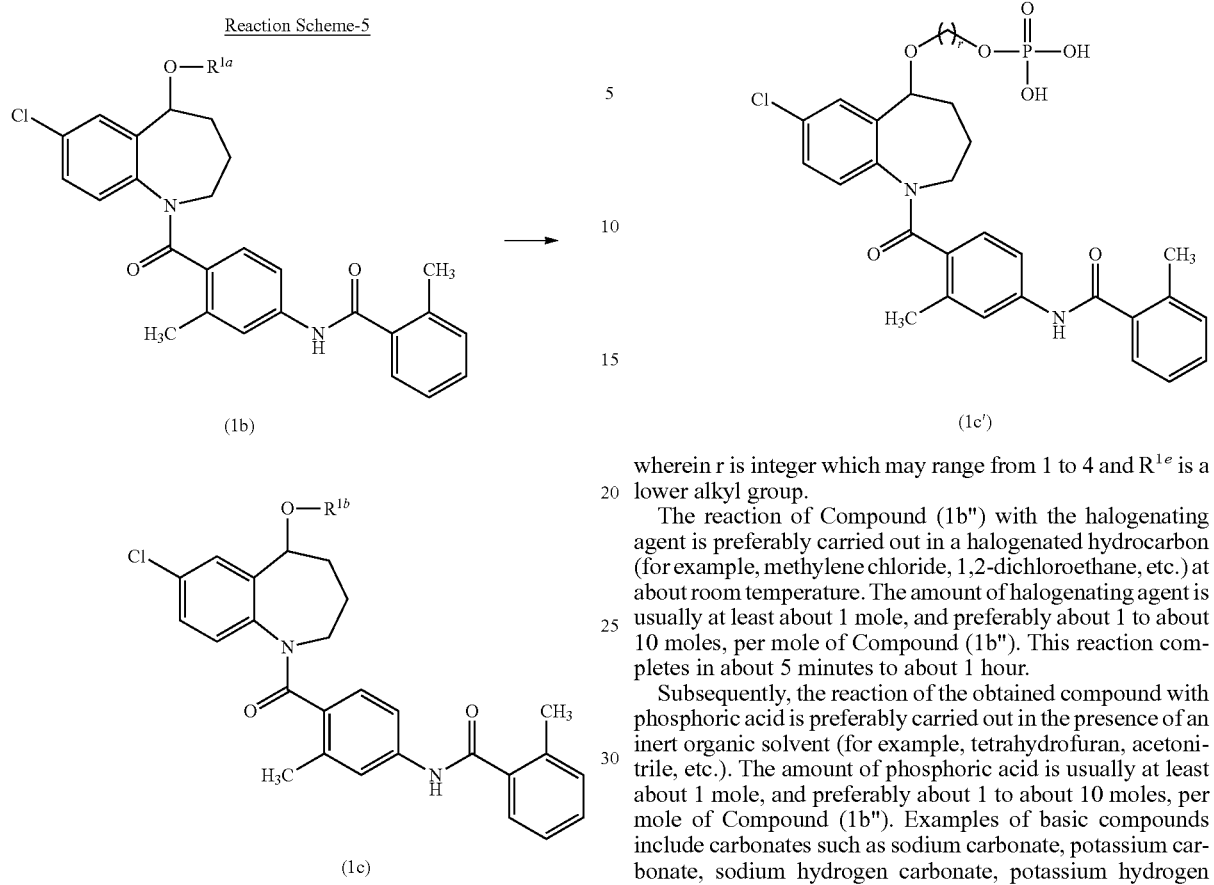

(1b)

(1c)

(1c')

wherein $R^{1b}$ is a lower alkyl group substituted with a dihydroxyphosphoryloxy group, and $R^{1a}$ is as defined above.

The process shown in Reaction Scheme-5 is a reaction to convert the lower alkyl group substituted with a lower alkylthio group of $R^1$ into a lower alkyl group substituted with a dihydroxyphosphoryloxy group. For example, to convert the methylthiomethyl group of $R^1$ into a dihydroxyphosphoryloxymethyl group, as shown in Reaction Scheme-5-1 below, Compound (1b") is reacted with a halogenating agent (for example, sulfuryl chloride, N-iodosuccinimide, etc.), and the obtained compound is then reacted with phosphoric acid in the presence of a basic compound.

wherein r is integer which may range from 1 to 4 and $R^{1e}$ is a lower alkyl group.

The reaction of Compound (1b") with the halogenating agent is preferably carried out in a halogenated hydrocarbon (for example, methylene chloride, 1,2-dichloroethane, etc.) at about room temperature. The amount of halogenating agent is usually at least about 1 mole, and preferably about 1 to about 10 moles, per mole of Compound (1b"). This reaction completes in about 5 minutes to about 1 hour.

Subsequently, the reaction of the obtained compound with phosphoric acid is preferably carried out in the presence of an inert organic solvent (for example, tetrahydrofuran, acetonitrile, etc.). The amount of phosphoric acid is usually at least about 1 mole, and preferably about 1 to about 10 moles, per mole of Compound (1b"). Examples of basic compounds include carbonates such as sodium carbonate, potassium carbonate, sodium hydrogen carbonate, potassium hydrogen carbonate, and cesium carbonate; phosphates such as potassium phosphate, and sodium phosphate; organic bases such as pyridine, imidazole, N-ethyldiisopropylamine, dimethylaminopyridine, triethylamine, trimethylamine, dimethylaniline, N-methylmorpholine, DBN, DBU, and DABCO; and mixtures thereof. The amount of basic compound is usually at least about 1 mole, and preferably about 1 to about 10 moles, per mole of Compound (1b"). The reaction temperature of the above reaction is usually room temperature to about 200° C., and preferably about 50° C. to about 150° C. The reaction usually completes in about 10 minutes to about 10 hours.

Among the benzazepine compounds represented by general formula (1) or salts thereof, Compound (1d) wherein $R^1$ is a group of (1-6) above (a lower alkyl group substituted with a lower alkanonyloxy group) can be prepared, for example, from Compound (1b) by the process according to the following Reaction Scheme-6:

Reaction Scheme-5-1

Reaction Scheme-6

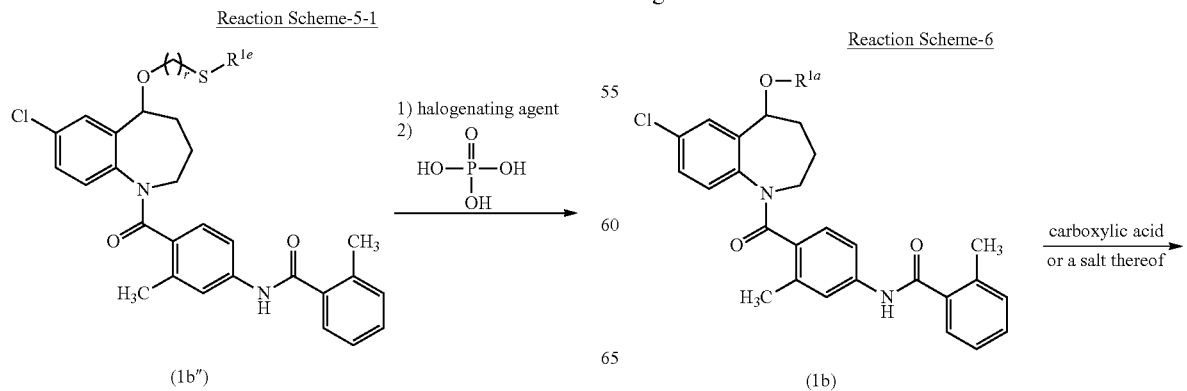

(1b")

(1b)

13

-continued

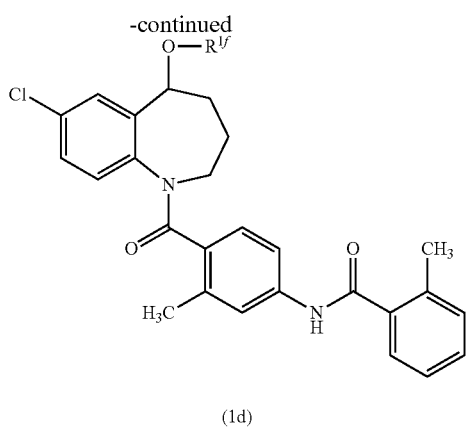

(1d)

wherein $R^{1f}$ is a lower alkyl group substituted with a lower alkanoyloxy group, and $R^{1a}$ is as defined above.

The process shown in Reaction Scheme-6 is a reaction to convert the lower alkyl group substituted with a lower alkylthio group of $R^1$ into a lower alkyl group substituted with a lower alkanoyloxy group. For example, as shown in Reaction Scheme-6-1 below, Compound (1b″) is reacted with a halogenating agent (for example, sulfuryl chloride, N-iodosuccinimide, etc.), and the obtained compound is then reacted with carboxylic acid or a salt thereof.

Reaction Scheme-6-1

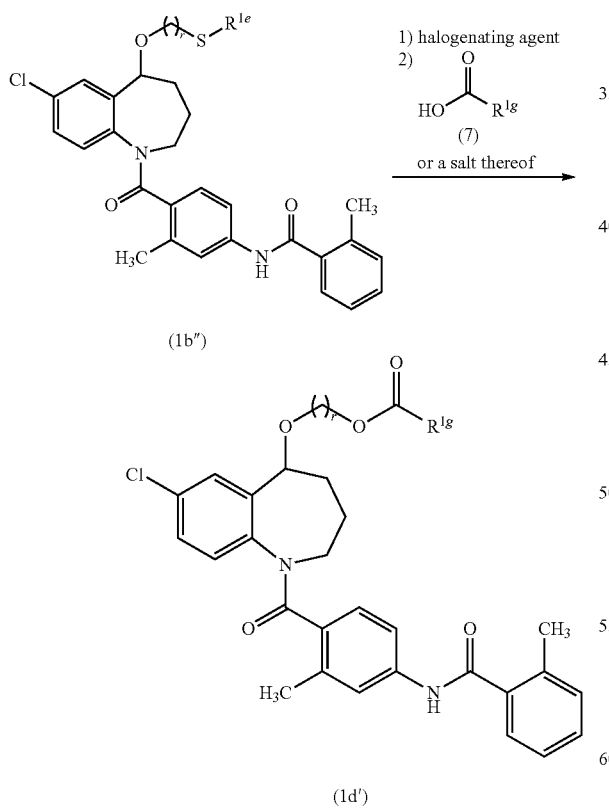

wherein $R^{1g}$ is a lower alkyl group and $R^{1e}$ are as defined above.

The reaction of Compound (1b″) with the halogenating agent is preferably carried out in a halogenated hydrocarbon

14

(for example, methylene chloride, 1,2-dichloroethane, etc.) at about room temperature. The amount of halogenating agent is usually at least about 1 mole, and preferably about 1 to about 10 moles, per mole of Compound (1b″). This reaction completes in about 5 minutes to about 1 hour.

Subsequently, the reaction of the obtained compound with carboxylic acid or a salt thereof is preferably carried out in the presence of an inert organic solvent (for example, tetrahydrofuran, acetonitrile, etc.). The amount of carboxylic acid is usually at least about 1 mole, and preferably about 1 to about 10 moles, per mole of Compound (1b). The reaction temperature is usually room temperature to about 200° C., and preferably about 50° C. to about 150° C. The reaction time is usually about 10 minutes to about 10 hours.

Among the benzazepine compounds represented by general formula (1) or salts thereof, Compound (1f) wherein $R^1$ is a group of (1-1) above, and $R^2$ is a group of (2-2) above can be prepared from Compound (1e) wherein $R^1$ is a group of (1-1) above, and $R^2$ is a group of (2-1) above by the process according to the following Reaction Scheme-7:

Reaction Scheme-7

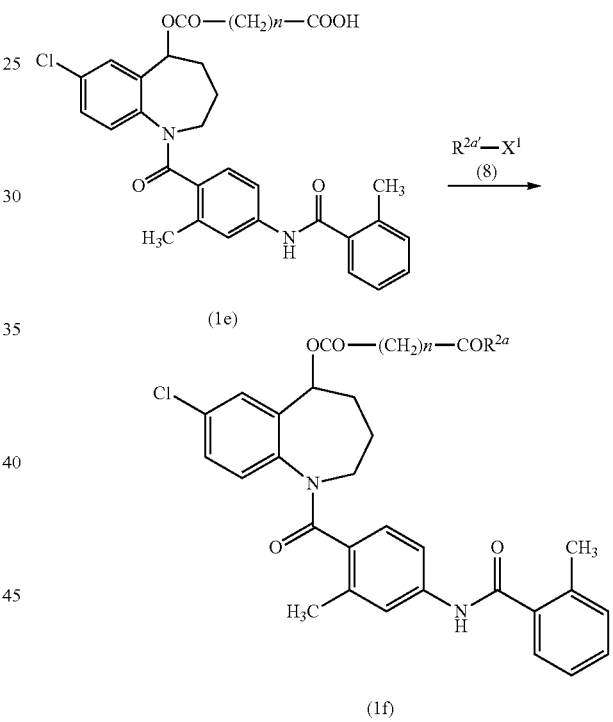

wherein $R^{2a}$ is a lower alkoxy group optionally substituted with a hydroxy, lower alkanoyl, lower alkanoyloxy, lower alkoxycarbonyloxy, cycloalkyloxycarbonyloxy, or 5-methyl-2-oxo-1,3-dioxol-4-yl group, $R^{2a\prime}$ is a lower alkoxy group optionally substituted with a hydroxy, lower alkanoyl, lower alkanoyloxy, lower alkoxycarbonyloxy, cycloalkyloxycarbonyloxy, or 5-methyl-2-oxo-1,3-dioxol-4-yl group, and n and $X^1$ are as defined above.

The reaction of Compound (1e) with Compound (8) is carried out in the presence of a basic compound in a suitable solvent.

The amount of compound (8) is usually about 1 mole to a large excess, and preferably about 1 to about 10 moles, per mole of Compound (1e).

Examples of reaction solvents include ethers such as diethyl ether, dioxane, tetrahydrofuran, monoglyme, and diglyme; halogenated hydrocarbons such as methylene chloride, chloroform, 1,2-dichloroethane, and carbon tetrachloride; esters such as ethyl acetate; aromatic hydrocarbons such as benzene, toluene, and xylene; aprotic polar solvents such as acetonitrile, DMF, DMSO, and NMP; and mixed solvents thereof.

Examples of basic compounds include carbonates such as sodium carbonate, potassium carbonate, sodium hydrogen carbonate, potassium hydrogen carbonate, and cesium carbonate; phosphates such as potassium phosphate, and sodium phosphate; organic bases such as pyridine, imidazole, N-ethyldiisopropylamine, dimethylaminopyridine, triethylamine, trimethylamine, dimethylaniline, N-methylmorpholine, DBN, DBU, and DABCO; and the like. Such compounds can be used singly or in a combination of two or more. The amount of basic compound is usually at least about 1 mole, and preferably about 1 to about 10 moles, per mole of Compound (1e). Such a basic compound can also be used as the solvent.

The reaction temperature is usually room temperature to 150° C., and preferably room temperature to 100° C. The reaction time is usually 15 minutes to 24 hours, preferably 30 minutes to 6 hours, and more preferably 1 to 3 hours.

Among the benzazepine compounds represented by general formula (1) or salts thereof, Compound (1g) wherein $R^1$ is a group of (1-1) above, and $R^2$ is an amino group substituted with one or more hydroxy-lower alkyl groups, can be prepared, for example, from Compound (1e) wherein $R^1$ is a group of (1-1) above, and $R^2$ is a group of (2-1) above by the process according to the following Reaction Scheme-8:

Reaction Scheme-8

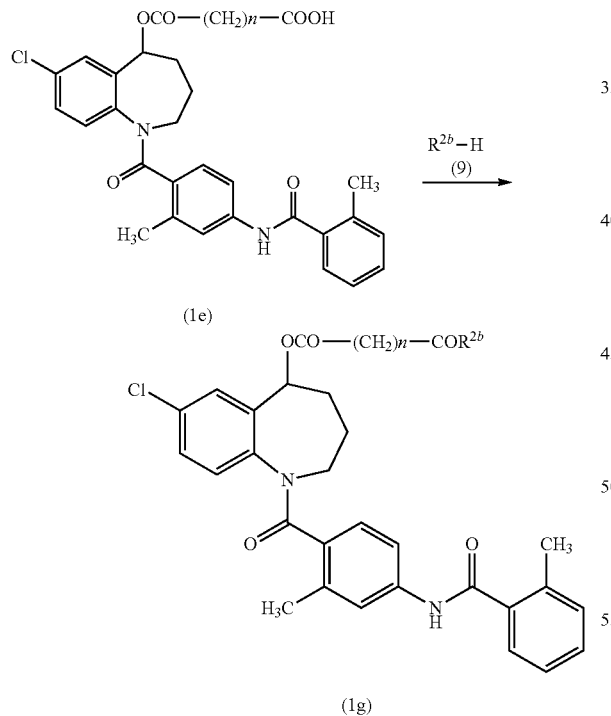

wherein $R^{2b}$ is an amino group substituted with one or more hydroxy-lower alkyl groups, and n is as defined above.

The reaction of Compound (1e) with Compound (9) is carried out under reaction conditions commonly used for the carbodiimide method. More specifically, Compound (1e) is condensed with Compound (9) in the presence of an activator such as dicyclohexylcarbodiimide, 1-(3-dimethylaminopropyl)-3-ethylcarbodiimide (WSC), or carbonyldiimidazole.

The amount of activator is usually at least about 1 mole, and preferably about 1 to about 5 moles, per mole of Compound (1e).

The condensation reaction is carried out in a suitable solvent in the presence or absence of a basic compound. Examples of solvents that can be used include ethers such as diethyl ether, dioxane, tetrahydrofuran, monoglyme, and diglyme; halogenated hydrocarbons such as methylene chloride, chloroform, 1,2-dichloroethane, and carbon tetrachloride; esters such as ethyl acetate; aromatic hydrocarbons such as benzene, toluene, and xylene; aprotic polar solvents such as acetonitrile, DMF, DMSO, and NMP; and mixed solvents thereof.

Examples of basic compounds include triethylamine, pyridine, and the like. The amount of basic compound is usually at least about 1 mole, and preferably about 1 to about 10 moles, per mole of Compound (1e). Such a basic compound can also be used as the solvent.

When WSC is used as an activator in the above reaction, the presence of a catalyst, such as 1-hydroxybenzotriazole (HOBt), in the reaction system can promote the reaction.

The reaction is usually carried out at about −20° C. to about 180° C., and preferably about 0° C. to about 150° C. The reaction usually completes in about 5 minutes to about 90 hours.

Among the benzazepine compounds represented by general formula (1) or salts thereof, compounds in which the amino group is protected by a protecting group can be converted by deprotection into the corresponding compounds wherein the amino group is not protected by the protecting group, for example, by the process shown in the following Reaction Scheme-9:

Reaction Scheme-9

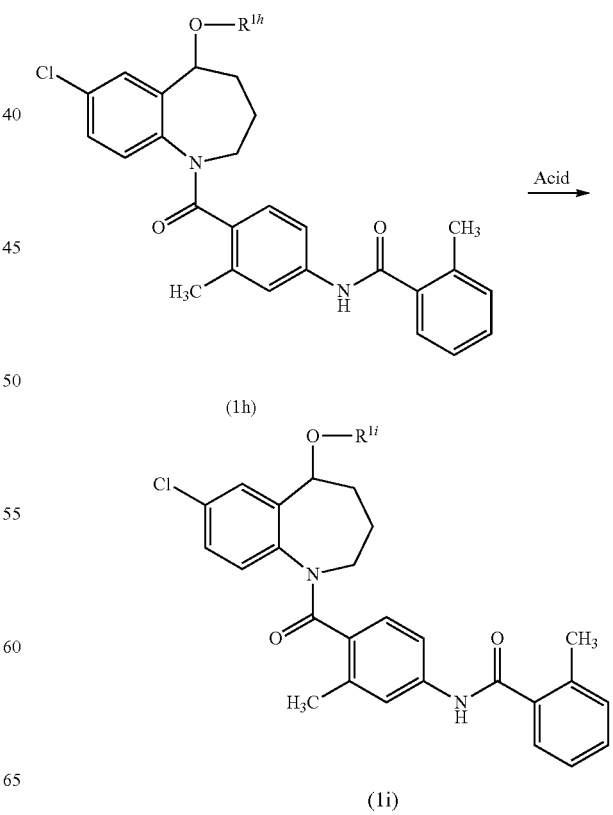

wherein $R^{1h}$ is the same as above $R^1$ having amino group, of which the said amino group is protected with an amino-protective group; $R^{1i}$ is the same as above $R^1$ having amino group corresponding to $R^{1h}$, of which the amino-protective group is deprotected.

The reaction of converting Compound (1 h) into Compound (1i) is carried out in the presence of an acid in a suitable solvent or without using any solvent.

Examples of solvents that can be used include water; lower alcohols such as methanol, ethanol, isopropanol, and tert-butanol; ketones such as acetone, and methyl ethyl ketone; ethers such as diethyl ether, dioxane, tetrahydrofuran, monoglyme, and diglyme; fatty acids such as acetic acid, and formic acid; esters such as methyl acetate, and ethyl acetate; halogenated hydrocarbons such as chloroform, dichloromethane, dichloroethane, and carbon tetrachloride; amides such as DMF, N,N-dimethylacetamide, and NMP; DMSO; hexamethylphosphoric triamide; and mixed solvents thereof.

Examples of acids include mineral acids such as hydrochloric acid, sulfuric acid, and hydrobromic acid; and organic acids, for example, carboxylic acids such as formic acid, acetic acid, and trifluoroacetic acid, and sulfonic acids such as p-toluenesulfonic acid.

The amount of acid is usually at least about 1 mole, and preferably about 1 to 10 moles, per mole of Compound (1 h). A large excess of acid can be used as the solvent.

The reaction is usually carried out at about 0° C. to about 200° C., and preferably at 0° C. to about 150° C. The reaction usually completes in about 10 minutes to about 30 hours.

Among the benzazepine compounds represented by general formula (1) or salts thereof, compounds having a halogen atom in $R^1$ can be reacted with an amine to convert the halogen atom into corresponding amino group, for example, by the process shown in the following Reaction Scheme-10:

wherein $R^{1j}$ is the same as above $R^1$ having halogen atom, and $R^{1k}$ is the group of which the halogen atom of $R^{1j}$ is converted to the amino group corresponding to the reactant amine.

The reaction of Compound (1j) with amine is carried out in a suitable inert solvent in the presence of a basic compound.

Examples of inert solvents include aromatic hydrocarbons such as benzene, toluene, and xylene; ethers such as diethyl ether, tetrahydrofuran, dioxane, monoglyme, and diglyme; halogenated hydrocarbons such as dichloromethane, dichloroethane, chloroform, and carbon tetrachloride; ketones such as acetone, and methyl ethyl ketone; acetonitrile, DMSO, DMF, hexamethylphosphoric triamide; and mixed solvents thereof.

Examples of basic compounds include carbonates such as sodium carbonate, potassium carbonate, sodium hydrogen carbonate, potassium hydrogen carbonate, and cesium carbonate; organic bases such as pyridine, imidazole, N-ethyldiisopropylamine, dimethylaminopyridine, triethylamine, trimethylamine, dimethylaniline, N-methylmorpholine, DBN, DBU, and DABCO. Such bases can be used singly or in a combination of two or more.

The amount of basic compound is usually at least about 1 mole, and preferably about 1 to about 10 moles, per mole of Compound (1j).

The amount of amine (8) is usually at least about 1 mole, and preferably about 1 to about 10 moles, per mole of Compound (1j).

Alkali metal halides such as sodium iodide and potassium iodide, and other compounds may be present in the reaction system of this reaction.

The reaction is usually carried out at about 0° C. to about 200° C., and preferably at 0° C. to about 150° C. The reaction usually completes in about 5 minutes to about 80 hours.

Among the benzazepine compounds represented by general formula (1) or salts thereof, compounds having an amino group in $R^1$ can be subjected to reductive alkylation to convert the amino group into a N-alkylamino group.

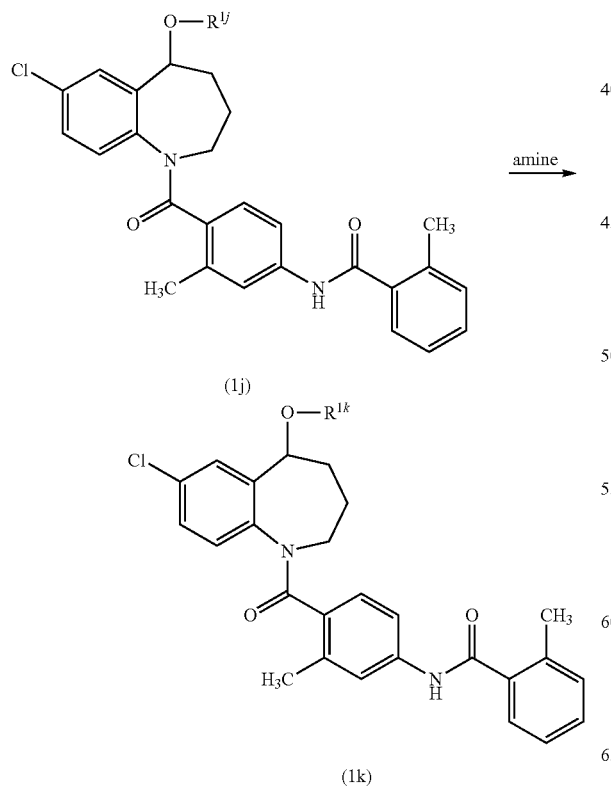

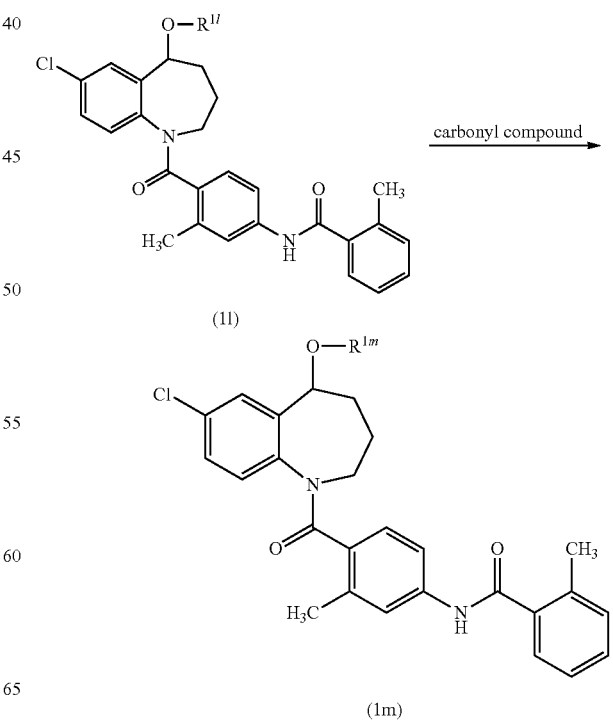

wherein $R^{1l}$ is the same as above $R^1$ having amino group, and $R^{1m}$ is the group of which the amino group of $R^{1l}$ is converted to the N-alkylamino group corresponding to the reactant carbonyl compound.

The reaction of Compound (11) with a carbonyl compound is carried out, for example, in the presence of a reducing agent without using any solvent or in a suitable solvent.

Examples of solvents that can be used include water; lower alcohols such as methanol, ethanol, isopropanol, n-butanol, tert-butanol, and ethylene glycol; acetonitrile; fatty acids such as formic acid and acetic acid; ethers such as diethyl ether, tetrahydrofuran, dioxane, monoglyme, and diglyme; aromatic hydrocarbons such as benzene, toluene, and xylene; halogenated hydrocarbons such as dichloromethane, dichloroethane, chloroform, and carbon tetrachloride; and mixed solvents thereof.

Examples of reducing agents include fatty acids such as formic acid; fatty acid alkali metal salts such as sodium formate, and sodium acetate; hydride reducing agents such as sodium borohydride, sodium cyanoborohydride, and sodium triacetyloxyborohydride; mixtures of such hydride reducing agents; catalytic hydrogenation reducing agents such as palladium black, palladium carbon, platinum oxide, platinum black, and Raney nickel: and the like.

When a fatty acid such as formic acid, or a fatty acid alkali metal salt such as sodium formate or sodium acetate is used as the reducing agent, the reaction temperature is preferably room temperature to about 200° C., and preferably about 50° C. to about 150° C. The reaction usually completes in about 10 minutes to about 10 hours. The amount of fatty acid or fatty acid alkali metal salt is preferably a large excess relative to Compound (11).

When a hydride reducing agent is used, the reaction temperature is usually about −80° C. to about 100° C., preferably about −80° C. to about 70° C. The reaction usually completes in about 30 minutes to about 60 hours. The amount of hydride reducing agent is usually about 1 to about 20 moles, and preferably about 1 to about 6 moles, per mole of Compound (11).

Amines such as trimethylamine, triethylamine, and N-ethyldiisopropylamine, or molecular sieves such as molecular sieves 3A (MS-3A), and molecular sieves 4A (MS-4A) may be added to this reaction system.

When a catalytic hydrogen reducing agent is used, the reaction is usually carried out at normal pressure to about 20 atm, and preferably at normal pressure to about 10 atm, in a hydrogen atmosphere or in the presence of a hydrogen donor, such as formic acid, ammonium formate, cyclohexene, or enhydrous hydrazine. The reaction temperature is usually about −30° C. to about 100° C., and preferably about 0° C. to about 60° C. The reaction usually completes in about 1 to about 12 hours. The amount of catalytic hydrogen reducing agent is usually about 0.1 to about 40 wt. %, and preferably about 1 to about 20 wt. %, relative to Compound (11).

The amount of Compound (9) used in the reaction of Compound (11) with Compound (9) is usually at least 1 mole, and preferably 1 mole to a large excess, per mole of Compound (11).

Among the benzazepine compounds represented by general formula (1) or salts thereof, compounds wherein $R^1$ is —CO—$(CH_2)_m$—$NR^3R^4$, and $R^4$ is (4-3) a lower alkoxycarbonyl group optionally substituted with a halogen atom, a lower alkanoyloxy group, or 5-methyl-2-oxo-1,3-dioxol-4-yl can be prepared by reacting the compounds, wherein $R^4$ is (4-1) a hydrogen atom, with an acid halide (10) by the process according to the following Reaction Scheme-12:

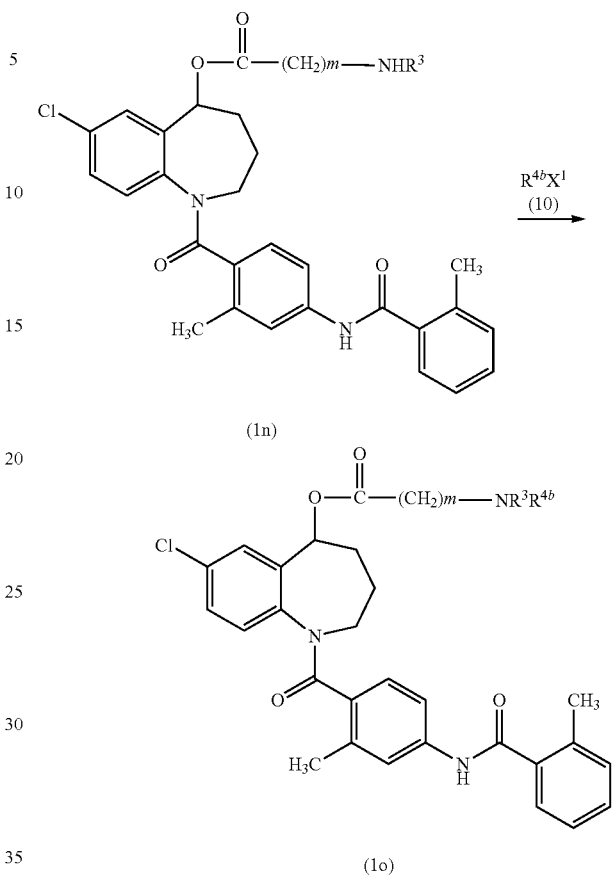

Reaction Scheme-12 wherein $R^{4b}$ is a lower alkoxycarbonyl group optionally substituted with a halogen atom, a lower alkanoyloxy group, or 5-methyl-2-oxo-1,3-dioxol-4-yl, and $R^3$, m, and $X^1$ are as defined above.

The reaction of Compound (1n) with an acid halide (10) is carried out in a suitable solvent in the presence of a basic compound.

The amount of acid halide (10) is usually 1 mole to a large excess, and preferably 1 to 10 moles, per mole of Compound (1n).

Examples of reaction solvents include ethers such as diethyl ether, dioxane, tetrahydrofuran, monoglyme, and diglyme; halogenated hydrocarbons such as methylene chloride, chloroform, 1,2-dichloroethane, and carbon tetrachloride; esters such as ethyl acetate; aromatic hydrocarbons such as benzene, toluene, and xylene; aprotic polar solvents such as acetonitrile, DMF, DMSO, and NMP; and mixed solvents thereof.

Examples of basic compounds include carbonates such as sodium carbonate, potassium carbonate, sodium hydrogen carbonate, potassium hydrogen carbonate, and cesium carbonate; phosphates such as potassium phosphate, and sodium phosphate; and organic bases such as pyridine, imidazole, N-ethyldiisopropylamine, dimethylaminopyridine, triethylamine, trimethylamine, dimethylaniline, N-methylmorpholine, DBN, DBU, and DABCO.

The amount of basic compound is usually at least about 1 mole, and preferably about 1 to about 10 moles, per mole of Compound (1n). Such an organic base can also be used as the solvent.

When a catalyst such as 4-dimethylaminopyridine is present in the reaction system in the above reaction, the reaction can be promoted.

The reaction temperature of the above reaction is usually −10° C. to 100° C., preferably 0° C. to 50° C., and more preferably 0° C. to room temperature. The reaction time is usually 15 minutes to 24 hours, preferably 30 minutes to 6 hours, and more preferably 1 to 3 hours.

Among the benzazepine compounds represented by general formula (1) or salts thereof, $R^1$ is a —CO—$NHR^4$ group, and $R^4$ is (4-2) a lower alkyl group optionally substituted with a halogen atom, a lower alkylamino group, a lower alkoxycarbonyl group, or 5-methyl-2-oxo-1,3-dioxol-4-yl can be prepared by reacting Compound (2) with an isocyanate compound (11) by the process according to Reaction Scheme-13.

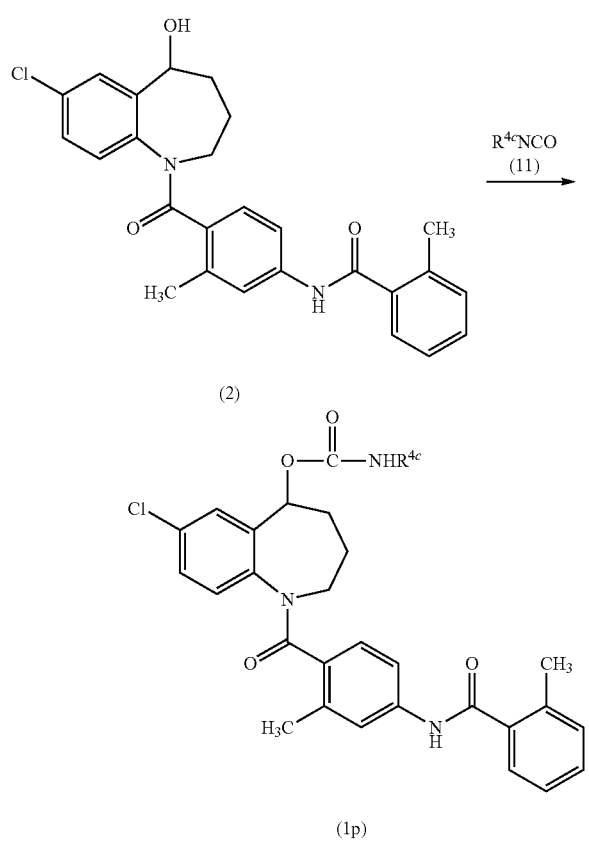

Reaction Scheme-13 wherein $R^{4c}$ is a lower alkyl group optionally substituted with a halogen atom, a lower alkylamino group, a lower alkoxycarbonyl group, or 5-methyl-2-oxo-1,3-dioxol-4-yl.

The reaction of Compound (2) with Compound (11) is carried out in the presence or absence of a basic compound, preferably in the absence of a basic compound, in a suitable inert solvent or without using any solvent.

Examples of inert solvents include aromatic hydrocarbons such as benzene, toluene, and xylene; ethers such as diethyl ether, tetrahydrofuran, dioxane, 2-methoxyethanol, monoglyme, and diglyme; halogenated hydrocarbons such as dichloromethane, dichloroethane, chloroform, and carbon tetrachloride; esters such as ethyl acetate, and methyl acetate; ketones such as acetone, and methyl ethyl ketone; acetonitrile, pyridine, DMSO, DMF, hexamethylphosphoric triamide; and mixed solvents thereof.

Examples of basic compounds include triethylamine, pyridine, and the like. The amount of basic compound is usually at least about 1 mole, and preferably about 1 to about 10 moles, per mole of Compound (2). Such a basic compound can also be used as the solvent.

The amount of Compound (11) is usually about 1 to about 5 moles, and preferably about 1 to 3 moles, per mole of Compound (2).

This reaction is usually carried out at about 0° C. to about 200° C., and preferably about room temperature to about 150° C. The reaction usually completes in about 5 minutes to about 30 hours.

When a catalyst such as 4-dimethylaminopyridine is present in the reaction system in the above reaction, the reaction can be promoted.

Compounds (2), (3), (4), (5), (6), (7), (8), (9), (10), (11), (1b), (1b"), (1e), (1 h), (1j), (11), (1n), carboxylic acids, amine, and carbonyl compound, which are used as starting materials in the above Reaction Schemes, are known compounds, or compounds that can be easily prepared according to known methods, such as the methods described in the Examples below.

Compounds (2), (3), (4), (5), (6), (7), (8), (9), (10), (11), (1b), (1b"), (1e), (1 h), (1j), (11), (1n), carboxylic acids, amine, and carbonyl compound, which are used as the starting materials in the above Reaction Schemes, may be in the form of suitable salts or reactive derivatives thereof. Examples of such suitable salts include salts mentioned above in Compound (1), such as sodium salts, potassium salts, cesium salts, and like alkali metal salts.

Compounds represented by general formula (1) of the present invention and salts thereof include stereoisomers, optical isomers, and solvates (hydrates, ethanolates, etc.) thereof.

Among the benzazepine compounds represented by general formula (1) of the invention, compounds having a basic group can be easily converted into acid addition salts by reacting the compounds with pharmaceutically acceptable acids. Examples of such salts include inorganic acid salts such as hydrochloride, sulphate, phosphate, hydrobromate, hydriodate, and nitrate; organic acid salts such as acetate, oxalate, succinate, maleate, fumarate, malate, tartrate, citrate, malonate, methanesulfonate, benzoate, trifluoroacetate, benzensuplhonate, formate, and toluenesulfonate; and amino acid salts (for example, arginate, aspartate, glutamate, etc.).

Among the benzazepine compounds represented by general formula (1) of the invention, compounds having an acidic group can be easily converted into salts with a base by reacting the compounds with pharmaceutically acceptable basic compounds. Examples of such salts include metal salts such as alkali metal salts (for example, sodium salts, potassium salts, etc.) and alkaline earth metal salts (for example, calcium salts, magnesium salts, etc.); ammonium salts; organic base salts (for example, trimethylamine salts, triethylamine salts, pyridine salts, picoline salts, dicyclohexylamine salts, N,N'-dibenzylethylenediamine salts, tris(hydroxymethyl) aminomethane salts, etc.); and the like. Examples of basic compounds include sodium hydroxide, potassium hydroxide, calcium hydroxide, sodium carbonate, potassium hydrogen carbonate, sodium hydrogen carbonate, and the like.

These salts are included in the scope of the present invention.

Each of the object compounds obtained according to the above Reaction Schemes can be isolated and purified from the reaction mixture by, for example, after cooling, subjecting the reaction mixture to isolation procedures such as filtration, concentration, extraction, etc., to separate a crude reaction product followed by conventional purification procedures such as column chromatography, recrystallization, etc.

The compound of the present invention has, for example, vasopressin antagonism, vasodilatory activity, hypotensive activity, activity for inhibiting glucose release from the liver, mesangial cell growth inhibitory activity, aquaretic activity, and platelet aggregation inhibitory activity. The compound is useful as a vasodilator, hypotensor, aquaretic agent, and platelet aggregation inhibitor, and is effective in the prevention and treatment of hypertension, edema (e.g., cardiac edema, hepatic edema, renal edema, cerebral edema), abdominal dropsy, heart failure (e.g., severe heart failure), renal dysfunction, syndrome of inappropriate secretion of vasopressin (SIADH), liver cirrhosis, hyponatremia, hypokalemia, diabetes, circulatory insufficiency, polycystic kidney disease (PKD), and the like.

When administered to the human body as a medicine, the compound of the invention may be used simultaneously with or separately from other pharmaceutical drugs, such as vasopressin antagonists, ACE inhibitors, β-blocking agents, aquaretic agents, angiotensin II antagonists (ARB), and/or digoxin.

The compound of the invention can be used in the form of a general pharmaceutical composition. Such a pharmaceutical composition can be prepared by a conventional method using commonly used diluents and/or excipients, such as fillers, extending agents, binders, humectants, disintegrators, surfactants, and lubricants.

The form of the pharmaceutical composition containing the compound of the invention can be suitably selected depending on the purpose of the treatment. Examples thereof include tablets, pills, powders, solutions, suspensions, emulsions, granules, capsules, suppositories, injections (solutions, suspensions, etc.), ointments, and the like.

To form tablets, any of the various carriers conventionally known in this field can be widely used. Examples thereof include excipients such as lactose, white sugar, sodium chloride, glucose, urea, starch, calcium carbonate, kaolin, crystalline cellulose, and silicic acid; binders such as water, ethanol, propanol, simple syrup, glucose solutions, starch solutions, gelatin solutions, carboxymethylcellulose, shellac, methylcellulose, potassium phosphate, and polyvinylpyrrolidone; disintegrators such as dry starch, sodium alginate, agar powder, laminaran powder, sodium hydrogen carbonate, calcium carbonate, fatty acid esters of polyoxyethylene sorbitan, sodium lauryl sulfate, stearic acid monoglycerides, starch, and lactose; disintegration inhibitors such as white sugar, stearin, cacao butter, and hydrogenated oils; absorbing agents such as quaternary ammonium bases, and sodium lauryl sulfate; wetting agents such as glycerol, and starch; adsorbents such as starch, lactose, kaolin, bentonite, and colloidal silicic acid; lubricants such as purified talc, stearates, boric acid powder, and polyethylene glycol; and the like. Further, such tablets may be tablets provided with typical coating as required, for example, sugar-coated tablets, gelatin encapsulated tablets, enteric-coated tablets, film-coated tablets, double- or multi-layered tablets, etc.

To form pills, any of the various carriers conventionally known in this field can be widely used. Examples thereof include excipients such as glucose, lactose, starch, cacao butter, hydrogenated vegetable oils, kaolin, and talc; binders such as gum arabic powder, tragacanth powder, gelatin, and ethanol; disintegrators such as laminarin, and agar; and the like.

To form suppositories, any of the various carriers conventionally known in this field can be widely used. Examples thereof include polyethylene glycol, cacao butter, higher alcohols, esters of higher alcohols, gelatin, semi synthetic glycerides, and the like.

Capsules can be prepared according to a conventional method by mixing the active ingredient compound with various carriers as mentioned above and filling the mixture into a hard gelatin capsule, soft gelatin capsule, or the like.

To form injections, solutions, emulsions, and suspensions are preferably sterilized and isotonic to the blood. When injections are prepared in the form of solutions, emulsions and suspensions, any of the diluents commonly employed in this field can be used. Examples of such diluents include water, aqueous lactic acid solutions, ethyl alcohol, propylene glycol, ethoxylated isostearyl alcohol, polyoxylated isostearyl alcohol, polyoxyethylene sorbitan fatty acid esters, and the like. In this case, isotonizing agents such as sodium chloride, glucose, mannitol, and glycerol in an amount sufficient to prepare an isotonic solution may be incorporated into the pharmaceutical composition. Commonly used pH adjusters, solubilizers, buffers, smoothing agents, and the like may also be added.

Other additives such as coloring agents, preservatives, flavors, and sweetening agents, and other medicines can also be added, if necessary.

The amount of compound represented by general formula (1) or salt thereof in the pharmaceutical preparation of the invention is not particularly limited, and can be suitably selected from a wide range. In general, the proportion of the compound is preferably about 0.01 to about 70 wt. % of the pharmaceutical preparation.

The way of administration of the pharmaceutical preparation of the invention is not particularly limited, and can be administered by a method suitable to the form of the preparation, the patient's age, sex and other conditions, and the severity of the disease. For example, tablets, pills, solutions, suspensions, emulsions, granules, and capsules are administered orally. Injections are intravenously administered singly or as mixed with typical replacement fluid such as glucose solutions, amino acid solutions, or the like, or singly administered intramuscularly, intracutaneously, subcutaneously or intraperitoneally, as required.

The dosage of the pharmaceutical preparation of the invention is suitably selected according to the dosage regimen, the patient's age, sex and other conditions, and the severity of the disease. The dosage is usually such that the compound represented by general formula (1), which is an effective ingredient, is administered in an amount of 0.001 to 100 mg, and preferably 0.001 to 50 mg, per kg of body weight per day in one or more administrations.

The dosage varies with various conditions. A dosage smaller than the above range may be sufficient, while a dosage larger than the above range may be necessary.

The patents, patent applications, and documents cited herein are incorporated by reference.

EFFECT OF THE INVENTION

According to the present invention, a novel benzazepine compound that has excellent properties, such as the maintenance of the blood level of tolvaptan for a long period of time enabling to provide the desired pharmaceutical effects, can be provided.

When administered into the human body, Compound (1) of the invention or a salt thereof can be easily converted into tolvaptan, which is an active ingredient.

Further, Compound (1) of the invention or a salt thereof is readily crystallized and easy to handle. Furthermore, Compound (1) of the invention or a salt thereof has excellent chemical stability.

A composition that can provide pharmaceutical effects equivalent to that of a useful drug tolvaptan can be provided in various forms by using Compound (1) of the invention or a salt thereof.

BEST MODE FOR CARRYING OUT THE INVENTION

The following examples illustrate the present invention in further detail.

EXAMPLE 1

{7-Chloro-1-[2-methyl-4-(2-methyl-benzoylamino)-benzoyl]-2,3,4,5-tetrahydro-1H-benzo[b]azepin-5-yl} Succinate Tolvaptan (1.0 g, 2.2 mmol), succinic anhydride (0.33 g, 3.3 mmol), and 4-dimethylaminopyridine (DMAP) (27 mg, 0.22 mmol) were added to 1-methyl-2-pyrolidone (3 ml), and the mixture was stirred at 100° C. for 1 hour. Water was added to the reaction mixture, and the resulted precipitates were collected by filtration. The precipitates were purified using silica gel flash chromatography (n-hexane:ethyl acetate=50: 50→20:80). The purified product was concentrated under reduced pressure. The residue was dissolved in aqueous acetonitrile, and then freeze-dried to obtain 300 mg of {7-chloro-1-[2-methyl-4-(2-methyl-benzoylamino)-benzoyl]-2,3,4,5-tetrahydro-1H-benzo[b]azepin-5-yl}succinate as white amorphous solid.

$^1$H-NMR (DMSO-$d_6$, 100° C.) δppm:
1.6-2.1 (4H, m), 2.37 (6H, s), 2.5-2.6 (2H, m), 2.6-2.7 (2H, m), 3.0-4.3 (2H, m), 5.9-6.0 (1H, m), 6.8-7.1 (2H, m), 7.1-7.3 (3H, m), 7.3-7.5 (4H, m), 7.56 (1H, s), 9.8 (1H, br).

EXAMPLE 2

Sodium {7-chloro-1-[2-methyl-4-(2-methylbenzoylamino)benzoyl]-2,3,4,5-tetrahydro-1H-benzo[b]azepin-5-yl} Succinate A sodium hydrogen carbonate (46 mg, 0.55 mmol) aqueous solution (2 ml) was added to a methanol solution (2 ml) of {7-chloro-1-[2-methyl-4-(2-methylbenzoylamino)benzoyl]-2,3,4,5-tetrahydro-1H-benzo[b]azepin-5-yl}succinate (0.30 g, 0.55 mmol), and the mixture was stirred at room temperature for 1 hour. Methanol was distilled off under reduced pressure at about 30° C. The resulting solution was freeze-dried to obtain 0.29 g (94%) of sodium {7-chloro-1-[2-methyl-4-(2-methylbenzoylamino)benzoyl]-2,3,4,5-tetrahydro-1H-benzo[b]azepin-5-yl} succinate as amorphous.

$^1$H-NMR (DMSO-$d_6$, 100° C.) δppm:
1.70-2.10 (4H, m), 2.19 (2H, t, J=7.1 Hz), 2.37 (6H, s), 2.56 (2H, t, J=7.1 Hz), 3.05-3.50 (1H, m), 3.65-4.25 (1H, m), 5.85-5.95 (1H, m), 6.75-6.90 (1H, m), 6.90-7.10 (2H, m), 7.15-7.55 (6H, m), 7.58 (1H, s), 9.80 (1H, br).

EXAMPLE 3

Potassium {7-chloro-1-[2-methyl-4-(2-methylbenzoylamino)benzoyl]-2,3,4,5-tetrahydro-1H-benzo[b]azepin-5-yl} Succinate Amorphous of potassium {7-chloro-1-[2-methyl-4-(2-methylbenzoylamino)benzoyl]-2,3,4,5-tetrahydro-1H-benzo[b]azepin-5-yl}succinate was obtained in a similar manner as in the above Example 2.

$^1$H-NMR (DMSO-$d_6$, 100° C.) δppm:
1.70-2.10 (4H, m), 2.16 (2H, t, J=7.1 Hz), 2.37 (6H, s), 2.48 (2H, t, J=7.1 Hz), 2.95-3.50 (1H, m), 3.70-4.25 (1H, m), 5.85-5.95 (1H, m), 6.75-6.90 (1H, m), 7.00-7.15 (2H, m), 7.20-7.45 (6H, m), 7.58 (1H, s), 9.77 (1H, br).

EXAMPLE 4

Sodium 4-{7-chloro-1-[2-methyl-4-(2-methylbenzoylamino)benzoyl]-2,3,4,5-tetrahydro-1H-benzo[b]azepin-5-yloxycarbonyl}Butyrate 4-{7-Chloro-1-[2-methyl-4-(2-methylbenzoylamino)benzoyl]-2,3,4,5-tetrahydro-1H-benzo[b]azepin-5-yloxycarbonyl}butyric acid (0.30 g, 0.53 mmol) was dissolved in acetone (2 ml). A sodium hydrogen carbonate (45 mg, 0.53 mmol) aqueous solution (2 ml) was added thereto and the mixture was stirred at room temperature for 1 hour. The reaction mixture was concentrated, and the residue was washed with ethyl acetate and then air-dried to obtain 0.14 g (45%) of sodium 4-{7-chloro-1-[2-methyl-4-(2-methylbenzoylamino)benzoyl]-2,3,4,5-tetrahydro-1H-benzo[b]azepin-5-yloxycarbonyl}butyrate as amorphous.

$^1$H-NMR (DMSO-$d_6$, 100° C.) δppm:
1.70-2.10 (8H, m), 2.37 (6H, s), 2.45-2.55 (2H, m), 3.10-3.55 (1H, m), 3.70-4.10 (1H, m), 5.90-6.00 (1H, m), 6.85-6.95 (1H, m), 7.00-7.10 (1H, m), 7.10-7.45 (7H, m), 7.58 (1H, s), 9.83 (1H, br).

EXAMPLE 5

{7-Chloro-1-[2-methyl-4-(2-methyl-benzoylamino)-benzoyl]-2,3,4,5-tetrahydro-1H-benzo[b]azepin-5-yl} Methyl Succinate Iodomethane (34 μl, 0.55 mmol) was added to a DMF (5 ml) suspension of {7-chloro-1-[2-methyl-4-(2-methyl-benzoylamino)benzoyl]-2,3,4,5-tetrahydro-1H-benzo[b]azepin-5-yl}succinate (0.25 g, 0.46 mmol) and potassium carbonate (76 mg, 0.55 mmol), and the mixture was stirred at room temperature for 2 hours. Water was then added to the reaction mixture, and the resulted precipitates were collected by filtration and air-dried. The dried product was purified by silica gel chromatography (n-hexane:ethyl acetate). The purified product was crystallized from methanol/water to thereby obtain 0.20 g (77%) of {7-chloro-1-[2-methyl-4-(2-methyl-benzoylamino)-benzoyl]-2,3,4,5-tetrahydro-1H-benzo[b]azepin-5-yl} methyl succinate as white powder.

Melting point: 173.6-175.5° C.
$^1$H-NMR (DMSO-$d_6$, 100° C.) δppm:
1.70-2.05 (4H, m), 2.37 (6H, s), 2.55-2.70 (2H, m), 2.70-2.80 (2H, m), 3.10-3.45 (1H, m), 3.62 (3H, s), 3.80-4.10 (1H, m), 5.90-6.00 (1H, m), 6.80-7.00 (2H, m), 7.05-7.25 (3H, m), 7.30-7.45 (4H, m), 7.56 (1H, s), 9.79 (1H, br).

EXAMPLE 6

7-Chloro-5-[N-(2-hydroxy-ethyl)-succinamoyloxy]-1-[2-methyl-4-(2-methyl-benzoylamino)-benzoyl]-2,3,4,5-tetrahydro-1H-benzo[b]azepine {7-Chloro-1-[2-methyl-4-(2-methyl-benzoylamino)benzoyl]-2,3,4,5-tetrahydro-1H-benzo[b]azepin-5-yl}succinate (0.30 g, 0.55 mmol), 2-aminoethanol(40 μl, 0.66 mmol), WSC (0.13 g, 0.66 mmol), and 1-hydroxybenzotriazole (HOBt) (0.10 g, 0.66 mmol) were dissolved in DMF (5 ml), and the mixture was stirred out at room temperature over night. Water was then added to the reaction mixture. The resulted precipitates were collected by filtration and air-dried. The dried product was purified by basic silica gel chromatography (ethyl acetate:methanol) to thereby obtain 0.19 g (59%) of 7-chloro-5-[N-(2-hydroxy-ethyl)-succinamoyloxy]-1-[2-methyl-4-(2-methyl-benzoylamino)-benzoyl]-2,3,4,5-tetrahydro-1H-benzo[b]azepine as amorphous.

$^1$H-NMR (CDCl$_3$) δppm:
1.25-2.90 (12H, m), 2.95-3.75 (7H, m), 4.60-4.95 (1H, m), 5.80-6.05 (1H, m), 6.35-6.65 (2H, m), 6.80-7.05 (2H, m), 7.10-7.70 (8H, m), 8.00-8.25 (1H, m).

EXAMPLE 7

{7-Chloro-1-[2-methyl-4-(2-methyl-benzoylamino)-benzoyl]-2,3,4,5-tetrahydro-1H-benzo[b]azepin-5-yloxycarbonylmethylthio} Acetic acid (also known as: tolvaptan thiodiglycolic acid monoester)

Tolvaptan (1.0 g, 2.2 mmol) and 4-dimethylaminopyridine (27 mg, 0.22 mmol) were dissolved in pyridine (5 ml). Thiodiglycolic anhydride (2.9 g, 22 mmol) was added thereto, and the mixture was stirred at room temperature for 1 hour. 1N hydrochloric acid was added to the reaction mixture, and then the mixture was extracted with ethyl acetate. The organic layer was washed with 1N hydrochloric acid, dried over anhydrous sodium sulfate. After filtration and concentration under reduced pressure, the residue was purified by silica gel flash chromatography (dichloromethane:methanol=100:0→83:17), and the colored component was removed by silica gel column chromatography (ethyl acetate). The resultant was further purified by silica gel flash chromatography (n-hexane:ethyl acetate=50:50→0:100), and the purified product was concentrated under reduced pressure. The residue was dissolved in aqueous acetonitrile, and then freeze-dried to obtain 350 mg of {7-chloro-1-[2-methyl-4-(2-methyl-benzoylamino)-benzoyl]-2,3,4,5-tetrahydro-1H-benzo[b]azepin-5-yloxycarbonylmethylthio}acetic acid as white amorphous solid.

$^1$H-NMR (DMSO-d$_6$, 100° C.) δppm:
1.6-2.2 (4H, m), 2.4 (6H, s), 3.0-4.4 (2H, m), 3.39 (2H, s), 3.60 (2H, s), 5.8-6.0 (1H, m), 6.8-7.1 (2H, m), 7.2-7.5 (7H, m), 7.57 (1H, s), 9.8 (1H, br).

EXAMPLE 8

Methyl {7-chloro-1-[2-methyl-4-(2-methyl-benzoylamino)-benzoyl]-2,3,4,5-tetrahydro-1H-benzo[b]azepin-5-yloxycarbonylmethylthio}-acetate Tolvaptan (1.0 g, 2.2 mmol) and 4-dimethylaminopyridine (27 mg, 0.22 mmol) were dissolved in pyridine (5 ml). Thiodiglycolic anhydride (0.43 g, 3.3 mmol) was added thereto, and the mixture was stirred at room temperature over night. Thiodiglycolic anhydride (0.86 g, 6.5 mmol) was further added, and then the mixture was stirred at room temperature for 2 hours. 1N hydrochloric acid was added to the reaction mixture, then the mixture was extracted with ethyl acetate. The organic layer was washed with 1N hydrochloric acid, dried over anhydrous sodium sulfate. After filtration and concentration under reduced pressure, trimethylsilyldiazomethane was added to the residue, and the mixture was stirred at room temperature for 1 hour. The resultant mixture was further concentrated under reduced pressure, and the residue was purified by silica gel column chromatography (n-hexane:ethyl acetate=60:40→0:100). The purified product was concentrated under reduced pressure, the residue was dissolved in aqueous acetonitrile and then freeze-dried to obtain 880 mg of methyl {7-chloro-1-[2-methyl-4-(2-methyl-benzoylamino)-benzoyl]-2,3,4,5-tetrahydro-1H-benzo[b]azepin-5-yloxycarbonylmethylthio}-acetate as white amorphous solid.

$^1$H-NMR (DMSO-d$_6$, 100° C.) δppm:
1.5-1.9 (4H, m), 2.37 (6H, s), 2.8-4.3 (2H, m), 3.48 (2H, s), 3.61 (2H, s), 3.63 (3H, s), 5.9-6.1 (1H, m), 6.8-7.1 (2H, m), 7.1-7.3 (3H, m), 7.3-7.5 (4H, m), 7.57 (1H, s), 9.82 (1H, br).

EXAMPLE 9

Methyl {7-chloro-1-[2-methyl-4-(2-methyl-benzoylamino)-benzoyl]-2,3,4,5-tetrahydro-1H-benzo[b]azepin-5-yloxycarbonylmethylsulfonyl}-acetate Methyl{7-chloro-1-[2-methyl-4-(2-methyl-benzoylamino)-benzoyl]-2,3,4,5-tetrahydro-1H-benzo[b]azepin-5-yloxycarbonylmethylthio}-acetate (480 mg, 0.81 mmol) was dissolved in a methanol (5 ml) and water (2 ml). Oxone® (2KHSO$_5$/K$_2$SO$_4$/KHSO$_4$) (1.5 g, 2.4 mmol) was added thereto and the mixture was stirred at room temperature for 20 hours. Water was added to the reaction mixture and the mixture was extracted with ethyl acetate. The extract was dried over anhydrous sodium sulfate. After filtration and concentration under reduced pressure, the residue was purified by silica gel flash chromatography (n-hexane:ethyl acetate=50:50→20:80). The purified product was concentrated under reduced pressure, the residue was dissolved in aqueous acetonitrile and freeze-dried to obtain 200 mg of methyl {7-chloro-1-[2-methyl-4-(2-methyl-benzoylamino)-benzoyl]-2,3,4,5-tetrahydro-1H-benzo[b]azepin-5-yloxycarbonylmethylsulfonyl}-acetate as white amorphous solid.

$^1$H-NMR (DMSO-d$_6$, 100° C.) δppm:
1.5-1.9 (4H, m), 2.37 (6H, s), 2.8-4.3 (2H, m), 3.48 (2H, s), 3.61 (2H, s), 3.63 (3H, s), 5.9-6.1 (1H, m), 6.8-7.1 (2H, m), 7.1-7.3 (3H, m), 7.3-7.5 (4H, m), 7.57 (1H, s), 9.82 (1H, br).

EXAMPLE 10

{7-Chloro-1-[2-methyl-4-(2-methyl-benzoylamino)-benzoyl]-2,3,4,5-tetrahydro-1H-benzo[b]azepin-5-yl} Hexadecanoate Palmitoyl chloride (1.24 ml, 4.4 mmol) was added to a dichloromethane (20 ml) solution of tolvaptan (2.00 g, 4.4 mmol) and pyridine (0.40 ml, 5.0 mmol), and the mixture was stirred at room temperature over night. Water was added to the reaction mixture and the mixture was extracted with dichloromethane. The combined organic layer was washed with water and an aqueous saturated sodium chloride solution, and dried over magnesium sulfate. After filtration and concentration, the residue was purified by silica gel chromatography (n-hexane:ethyl acetate) to thereby obtain 2.25 g (74%) of {7-chloro-1-[2-methyl-4-(2-methyl-benzoylamino)-benzoyl]-2,3,4,5-tetrahydro-1H-benzo[b]azepin-5-yl}hexadecanoate as amorphous.

$^1$H-NMR (DMSO-d$_6$, 100° C.) δppm:
0.85 (3H, t, J=6.8 Hz), 1.15-1.45 (24H, m), 1.55-1.70 (2H, m), 1.75-2.10 (4H, m), 2.37 (6H, s), 2.40-2.50 (2H, m), 3.05-3.55 (1H, m), 3.60-4.30 (1H, m), 5.90-6.00 (1H, m), 6.80-7.05 (2H, m), 7.10-7.45 (7H, m), 7.56 (1H, s), 9.81 (1H, br).

EXAMPLE 11

{7-Chloro-1-[2-methyl-4-(2-methyl-benzoylamino)-benzoyl]-2,3,4,5-tetrahydro-1H-benzo[b]azepin-5-yl}chloroacetate Tolvaptan (10 g, 22 mmol) and pyridine (2.7 ml, 33 mmol) were suspended in dichloromethane (100 ml), and chloroacetyl chloride (2.6 ml, 33 mmol) was added dropwise under cooling with ice. The obtained mixture was stirred at room temperature for 1 hour. 1N hydrochloric acid was added to the reaction mixture, and the mixture was extracted with dichloromethane. The organic layer was washed with 1N hydrochloric acid, dried over anhydrous sodium sulfate. After filtration and concentration under reduced pressure, the residue was purified by silica gel flash chromatography (n-hexane:ethyl acetate=60:40→46:54). The purified product was concentrated under reduced pressure to obtain 12 g of {7-chloro-1-[2-methyl-4-(2-methyl-benzoylamino)-benzoyl]-2,3,4,5-tetrahydro-1H-benzo[b]azepin-5-yl}chloroacetate as white amorphous solid.

$^1$H-NMR (DMSO-$d_6$, 100° C.) δppm:
1.7-2.2 (4H, m), 2.36 (6H, s), 2.6-4.3 (2H, m), 4.44 (2H, s), 5.9-6.0 (1H, m), 6.8-7.1 (2H, m), 7.1-7.3 (3H, m), 7.3-7.5 (4H, m), 7.57 (1H, s), 9.8 (1H, br).

EXAMPLE 12 tert-Butyl 4-{7-chloro-1-[2-methyl-4-(2-methyl-benzoylamino)-benzoyl]-2,3,4,5-tetrahydro-1H-benzo[b]azepin-5-yloxycarbonylmethyl}-piperazine-1-carboxylate {7-Chloro-1-[2-methyl-4-(2-methyl-benzoylamino)benzoyl]-2,3,4,5-tetrahydro-1H-benzo[b]azepin-5-yl}chloroacetate (1.2 g, 2.3 mmol), tert-butyl piperazine-1-carboxylate (1-BOC-piperazine) (0.47 g, 2.5 mmol), and potassium carbonate (0.35 g, 2.5 mmol) were added to acetonitrile (10 ml), and the mixture was stirred at room temperature for 2 hours. Ethyl acetate was then added to the reaction mixture and the insoluble substance was removed by filtration. The filtrate was concentrated under reduced pressure, and the residue was purified by silica gel flash chromatography (n-hexane:ethyl acetate=50:50→20:80). The purified product was concentrated under reduced pressure to obtain 1.2 g of tert-butyl 4-{7-chloro-1-[2-methyl-4-(2-methyl-benzoylamino)-benzoyl]-2,3,4,5-tetrahydro-1H-benzo[b]azepin-5-yloxycarbonylmethyl}-piperazine-1-carboxylate as yellow oil.

$^1$H-NMR (DMSO-$d_6$, 100° C.) δppm:
1.42 (9H, s), 1.7-2.2 (4H, m), 2.39 (6H, s), 2.56 (4H, t, J=5.1 Hz), 3.37 (4H, t, J=5.1 Hz), 3.42 (2H, s), 2.6-4.3 (2H, m), 5.9-6.1 (1H, m), 6.9-7.0 (1H, m), 7.0-7.1 (1H, m), 7.1-7.5 (7H, m), 7.59 (1H, s), 9.8 (1H, br).

EXAMPLE 13

1-{7-Chloro-1-[2-methyl-4-(2-methyl-benzoylamino)-benzoyl]-2,3,4,5-tetrahydro-1H-benzo[b]azepin-5-yloxycarbonylmethyl}-piperazine dihydrochloride A 4N hydrogen chloride ethyl acetate solution (3.7 ml) was added to an ethyl acetate solution (15 ml) of tert-butyl 4-{7-chloro-1-[2-methyl-4-(2-methyl-benzoylamino)-benzoyl]-2,3,4,5-tetrahydro-1H-benzo[b]azepin-5-yloxycatbonylmethyl}-piperazine-1-carboxylate (1.2 g, 1.8 mmol), and the mixture was stirred at room temperature for 12 hours. The precipitates were collected by filtration, washed with ethyl acetate, and dried to obtain 800 mg of 1-{7-chloro-1-[2-methyl-4-(2-methyl-benzoylamino)-benzoyl]-2,3,4,5-tetrahydro-1H-benzo[b]azepin-5-yloxycarbonylmethyl}-piperazine dihydrochloride as yellow powder.

$^1$H-NMR (DMSO-$d_6$, 100° C.) δppm:
1.6-2.4 (4H, m), 2.369 (3H, s), 2.374 (3H, s), 2.8-3.0 (4H, m), 3.0-3.2 (4H, m), 3.4-3.7 (2H, m), 3.0-4.3 (2H, m), 5.7 (1H, br), 5.9-6.1 (1H, m), 6.8-7.1 (2H, m), 7.1-7.3 (3H, m), 7.3-7.5 (4H, m), 7.56 (1H, s), 9.2 (2H, br), 9.87 (1H, br).

EXAMPLE 14

1-{7-Chloro-1-[2-methyl-4-(2-methyl-benzoylamino)-benzoyl]-2,3,4,5-tetrahydro-1H-benzo[b]azepin-5-yloxycarbonylmethyl}-4-methyl-piperazine dihydrochloride 1-{7-Chloro-1-[2-methyl-4-(2-methyl-benzoylamino)-benzoyl]-2,3,4,5-tetrahydro-1H-benzo[b]azepin-5-yloxycarbonylmethyl}-piperazine dihydrochloride (400 mg, 0.62 mmol), formalin (0.15 ml, 1.9 mmol), sodium acetate (61 mg, 0.74 mmol), and sodium cyanotrihydroborate (119 mg, 1.9 mmol) were added to methanol (5 ml), and the mixture was stirred at room temperature for 1 hour. Water and aqueous sodium hydroxide solution were added to the reaction mixture, and the precipitates were collected by filtration, washed with water, and then dried. The obtained solid was dissolved in ethyl acetate, and a 4N hydrogen chloride ethyl acetate solution (0.5 ml) was added thereto. The precipitates were then collected by filtration, washed with ethyl acetate and dried to obtain 240 mg of 1-{7-chloro-1-[2-methyl-4-(2-methyl-benzoylamino)-benzoyl]-2,3,4,5-tetrahydro-1H-benzo[b]azepin-5-yloxycarbonylmethyl}-4-methyl-piperazine dihydrochloride as white powder.

$^1$H-NMR (DMSO-$d_6$, 100° C.) δppm:
1.6-2.1 (4H, m), 2.369 (3H, s), 2.374 (3H, s), 2.73 (3H, s), 2.8-4.3 (2H, m), 2.8-3.0 (4H, m), 3.0-3.4 (4H, m), 3.54 (2H, s), 5.9-6.1 (1H, m), 6.8-7.1 (2H, m), 7.1-7.4 (7H, m), 7.54 (1H, s), 9.8 (1H, br).

EXAMPLE 15

{7-Chloro-1-[2-methyl-4-(2-methyl-benzoylamino)-benzoyl]-2,3,4,5-tetrahydro-1H-benzo[b]azepin-5-yl}-4-dimethylaminobutyrate hydrochloride Tolvaptan (1.0 g, 2.2 mmol), 4-dimethylamino-butyric acid hydrochloride (0.48 g, 2.9 mmol), and 4-dimethylaminopyridine (27 mg, 0.22 mmol) were suspended in dichloromethane (5 ml). Triethylamine (0.4 ml) and 1-(3-dimethylaminopropyl)-3-ethylcarbodiimide hydrochloride (WSC) (0.55 g, 2.9 mmol) were added thereto, and the mixture was stirred at room temperature for 12 hours. An aqueous saturated sodium hydrogen carbonate solution was added to the reaction mixture, and the mixture was extracted with ethyl acetate. The organic layer was washed with an aqueous saturated sodium chloride solution, dried over anhydrous sodium sulfate. After filtration and concentration under reduced pressure, the residue was purified by silica gel flash chromatography (n-hexane:ethyl acetate=50:50→0:100). The purified product was concentrated under reduced pressure. The residue was then dissolved in ethyl acetate, a 4N hydrogen chloride ethyl acetate solution was added thereto, and the resultant mixture was concentrated under reduced pressure. To the residue was added water (10 ml). After filtration, the filtrate was freeze-dried to obtain 0.91 g of 7-chloro-1-[2-methyl-4-(2-methyl-benzoylamino)-benzoyl]-2,3,4,5-tetrahydro-1H-benzo[b]azepin-5-yl 4-dimethylaminobutyrate hydrochloride as white amorphous solid.

$^1$H-NMR (DMSO-d$_6$, 100° C.) δppm:
1.6-2.1 (6H, m), 2.37 (3H, s), 2.38 (3H, s), 2.5-2.6 (2H, m), 2.74 (6H, s), 3.0-3.1 (2H, m), 3.0-4.3 (2H, m), 5.9-6.0 (1H, m), 6.7-7.1 (2H, m), 7.1-7.2 (3H, m), 7.2-7.5 (4H, m), 7.54 (1H, s), 9.8 (1H, br).

EXAMPLE 16

7-Chloro-1-(2-methyl-4-(2-methylbenzamido)benzoyl)-2,3,4,5-tetrahydro-1H-benzo[b]azepin-5-yl 4-chlorobutyrate Tolvaptan (10.0 g, 22.3 mmol) was dispersed in dichloromethane (100 ml). Pyridine (2.7 ml) was added thereto, and the mixture was stirred. 4-Chlorobutyric acid chloride (3.74 ml) was gradually added to the obtained mixture, and the mixture was stirred at room temperature over night. The reactant was then poured into water, and the mixture was extracted with dichloromethane, washed with a sodium hydrogen sulfate aqueous solution, dried over magnesium sulfate. After filtration and concentration under reduced pressure, the resulted residue was crystallized with diethyl ether. The resulted crystals were collected by filtration, and dried to obtain 10.7 g of 7-chloro-1-[2-methyl-4-(2-methylbenzamido)benzoyl]-2,3,4,5-tetrahydro-1H-benzo[b]azepin-5-yl 4-chlorobutyrate as white powder.

$^1$H-NMR (CDCl$_3$) δppm:
1.50-2.92 (16H, m), 3.10-4.02 (2.4H, m), 4.70-5.13 (1H, m), 5.86-6.19 (1.2H, m), 6.48-6.68 (1H, m), 6.82-7.82 (8.8H, m).

EXAMPLE 17

7-Chloro-1-(2-methyl-4-(2-methylbenzamido)benzoyl)-2,3,4,5-tetrahydro-1H-benzo[b]azepin-5-yl 4-(4-acetylpiperazin-1-yl)butyrate 7-Chloro-1-(2-methyl-4-(2-methylbenzamido)benzoyl)-2,3,4,5-tetrahydro-1H-benzo[b]azepin-5-yl 4-chlorobutyrate (0.5 g) was dissolved in acetonitrile (10 ml). 1-Acetylpiperazine (0.35 g), sodium iodide (0.41 g), and sodium carbonate (0.19 g) were added to the solution, and the mixture was heated under reflux for 19 hours. The reactant was poured into water, and the mixture was extracted with ethyl acetate, washed with water, dried over sodium carbonate. After filtration and concentration under reduced pressure, the residue was purified by silica gel column chromatography (dichloromethane:methanol=100:1→100:10) to obtain 0.3 g of 7-chloro-1-(2-methyl-4-(2-methylbenzamido)benzoyl)-2,3,4,5-tetrahydro-1H-benzo[b]azepin-5-yl 4-(4-acetylpiperazin-1-yl)butyrate as colorless oil.

$^1$H-NMR (CDCl$_3$) δppm:
1.52-2.66 (23.6H, m), 2.70-2.92 (1H, m), 3.03-4.07 (4.4H, m), 4.72-5.14 (1H, m), 5.83-6.20 (1.2H, m), 6.45-6.68 (1H, m), 6.79-7.78 (8.8H, m).

EXAMPLE 18

7-Chloro-1-[2-methyl-4-(2-methylbenzamido)-benzoyl]-2,3,4,5-tetrahydro-1H-benzo[b]azepin-5-yl [(1-chloroethoxycarbonyl)methylamino]acetate 1-Chloroethyl chloroformate (0.12 ml, 1.2 mmol) was added dropwise to a dichloromethane (10 ml) solution of 7-chloro-1-[2-methyl-4-(2-methylbenzamido)benzoyl]-2,3,4,5-tetrahydro-1H-benzo[b]azepin-5-yl methylaminoacetate (0.60 g, 1.2 mmol), and the mixture was cooled with ice. Then N-methylmorpholine (0.15 ml, 1.4 mmol) was gradually added dropwise thereto. After the resultant mixture was stirred at room temperature for 1 hour, the reaction mixture was diluted with ethyl acetate, washed with water and an aqueous saturated sodium chloride solution, dried over sodium sulfate. After filtration and concentration, the residue was purified by silica gel chromatography (n-hexane:ethyl acetate) to obtain 0.67 g (93%) of 7-chloro-1-[2-methyl-4-(2-methylbenzamido)-benzoyl]-2,3,4,5-tetrahydro-1H-benzo[b]azepin-5-yl [(1-chloroethoxycarbonyl)methylamino]acetate as amorphous.

$^1$H-NMR (CDCl$_3$) δppm:
1.70-1.95 (5H, m), 2.10-2.55 (7H, m), 2.75-3.15 (4H, m), 3.85-4.55 (2H, m), 4.70-5.10 (1H, m), 5.85-6.20 (1H, m), 6.45-6.65 (2H, m), 6.75-7.75 (11H, m)
MS (M$^{+1}$): 626.

EXAMPLE 19

7-Chloro-1-[2-methyl-4-(2-methyl-benzoylamino)-benzoyl]-2,3,4,5-tetrahydro-1H-benzo[b]azepin-5-yl [(1-acetoxy-ethoxycarbonyl)methylamino]Actate N-methylmorpholine (0.31 ml, 2.8 mmol) was added dropwise to an acetic acid (0.32 ml, 5.6 mmol) solution of 7-chloro-1-[2-methyl-4-(2-methylbenzamido)benzoyl]-2,3,4,5-tetrahydro-1H-benzo[b]azepin-5-yl [(1-chloroethoxycarbonyl)methylamino]acetate (0.35 g, 0.56 mmol) under cooling with ice, and the mixture was stirred at room temperature for two days. Water was added to the reaction mixture, and then the resulted precipitates were collected by filtration and air-dried. The dried product was purified by silica gel chromatography (n-hexane:ethyl acetate) to obtain 0.26 g (72%) of 7-chloro-1-[2-methyl-4-(2-methyl-benzoylamino)-benzoyl]-2,3,4,5-tetrahydro-1H-benzo[b]azepin-5-yl [(1-acetoxy-ethoxycarbonyl)methylamino]acetate as amorphous.

$^1$H-NMR (DMSO-d$_6$) δppm:
1.35-1.45 (3H, m), 1.75-2.15 (7H, m), 2.37 (6H, s), 2.95 (3H, s), 3.15-3.50 (1H, m), 3.70-4.15 (1H, m), 4.17 (2H, s), 5.95-6.05 (1H, m), 6.55-6.70 (1H, m), 6.85-7.00 (2H, m), 7.10-7.25 (3H, m), 7.30-7.45 (4H, m), 7.56 (1H, s), 9.77 (1H, br).

EXAMPLE 20

7-Chloro-1-[2-methyl-4-(2-methyl-benzoylamino)-benzoyl]-2,3,4,5-tetrahydro-1H-benzo[b]azepin-5-yl 3-[2-(bis-benzyloxy-phosphoryloxy)-4,6-dimethyl-phenyl]-3-methyl-butyrate Tolvaptan (0.63 g), 3-[2-(bis-benzyloxy-phosphoryloxy)-4,6-dimethyl-phenyl]-3-methyl-butyric acid (0.70 g), and 4-dimethylaminopyridine (DMAP) (24 mg, 0.22 mmol) were suspended in dichloromethane (10 ml). N$^1$-((ethylimino)methylene)-N$^3$,N$^3$-dimethylpropane-1,3-diamine hydrochloride (WSC) (383 mg) was added thereto, and the mixture was stirred at room temperature for 3 hours. Water was added to the reaction mixture, and the mixture was extracted with ethyl acetate, dried over anhydrous sodium sulfate. After filtration and concentration under reduced pressure, the residue was purified by silica gel flash chromatography (n-hexane:ethyl acetate=70:30→35:65). The purified product was concentrated under reduced pressure to obtain 0.92 g of 7-chloro-1-

[2-methyl-4-(2-methyl-benzoylamino)-benzoyl]-2,3,4,5-tetrahydro-1H-benzo[b]azepin-5-yl 3-[2-(bis-benzyloxy-phosphoryloxy)-4,6-dimethyl-phenyl]-3-methyl-butyrate as white amorphous solid.

$^1$H-NMR (DMSO-d$_6$, 100° C.) δppm:
1.5-1.9 (7H, m), 2.10 (3H, s), 2.32 (3H, s), 2.36 (3H, s), 2.6-4.3 (2H, m), 2.91 (2H, d, J=15.3 Hz), 3.13 (2H, d, J=15.3 Hz), 5.11 (2H, s), 5.14 (2H, s), 5.7-5.9 (1H, m), 6.74 (1H, s), 6.75-7.4 (20H, m), 7.54 (1H, s), 9.8 (1H, br).

EXAMPLE 21

7-Chloro-1-[2-methyl-4-(2-methyl-benzoylamino)-benzoyl]-2,3,4,5-tetrahydro-1H-benzo[b]azepin-5-yl 3-(2,4-dimethyl-6-phosphonooxy-phenyl)-3-methyl-butyrate A mixture of 7-chloro-1-[2-methyl-4-(2-methylbenzoylamino)-benzoyl]-2,3,4,5-tetrahydro-1H-benzo[b]azepin-5-yl 3-[2-(bis-benzyloxy-phosphoryloxy)-4,6-dimethyl-phenyl]-3-methyl-butyrate (0.92 g) in ethyl acetate (10 ml) was hydrogenated over 5% platinum carbon (100 mg). The catalyst was removed by filtration through Celite layer, and the filtrate was concentrated under reduced pressure. The residue was purified by silica gel flash chromatography (dichloromethane:methanol=90:10→50:50). The purified product was concentrated under reduced pressure, and the aqueous acetonitrile solution of the residue was freeze-dried to obtain 0.21 g of 7-chloro-1-[2-methyl-4-(2-methyl-benzoylamino)-benzoyl]-2,3,4,5-tetrahydro-1H-benzo[b]azepin-5-yl 3-(2,4-dimethyl-6-phosphonooxy-phenyl)-3-methyl-butyrate as white amorphous solid.

$^1$H-NMR (DMSO-d$_6$, 100° C.) δppm:
1.60 (3H, s), 1.61 (3H, s), 1.6-2.0 (4H, m), 2.10 (3H, s), 2.34 (3H, s), 2.37 (3H, s), 2.42 (3H, s), 2.3-4.2 (2H, m), 2.9-3.4 (2H, m), 5.8-5.9 (1H, m), 6.45 (1H, s), 6.8-6.9 (1H, m), 6.9-7.0 (1H, s), 7.0-7.4 (7H, m), 7.43 (1H, d, J=7.4 Hz), 7.63 (s, 3H), 9.91 (1H, br).

EXAMPLE 22

Chloromethyl {7-chloro-1-[2-methyl-4-(2-methyl-benzoylamino)-benzoyl]-2,3,4,5-tetrahydro-1H-benzo[b]azepin-5-yl} Carbonate Tolvaptan (5.0 g) and pyridine (1.1 ml) were suspended in dichloromethane (50 ml). Chloromethyl chloroformate (1.1 ml) was added thereto under cooling with ice, and the mixture was stirred at room temperature for 30 minutes. The reaction mixture was washed with water, dried over anhydrous sodium sulfate. After filtration and concentration under reduced pressure, the residue was purified by silica gel flash chromatography (n-hexane:ethyl acetate=70:30→50:50). The purified product was concentrated under reduced pressure to obtain 6.1 g of chloromethyl {7-chloro-1-[2-methyl-4-(2-methyl-benzoylamino)-benzoyl]-2,3,4,5-tetrahydro-1H-benzo[b]azepin-5-yl} carbonate as white amorphous solid.

$^1$H-NMR (DMSO-d$_6$, 100° C.) δppm:
1.7-2.2 (4H, m), 2.36 (6H, s), 2.6-5.8 (2H, m), 5.9-6.0 (3H, m), 6.8-7.1 (2H, m), 7.1-7.5 (7H, m), 7.58 (1H, s), 9.8 (1H, br).

EXAMPLE 23

{7-chloro-1-[2-methyl-4-(2-methyl-benzoylamino)-benzoyl]-2,3,4,5-tetrahydro-1H-benzo[b]azepin-5-yl} iodomethyl carbonate Chloromethyl {7-chloro-1-[2-methyl-4-(2-methyl-benzoylamino)-benzoyl]-2,3,4,5-tetrahydro-1H-benzo[b] azepin-5-yl}carbonate (3.8 g) and sodium iodide (5.3 g) were added to acetone (27 ml), and then the mixture was heated under reflux for 3 hours. After cooling to room temperature, water was added thereto and the resulted precipitates were collected by filtration. The precipitates were washed with water, and dried to obtain 4.2 g of {7-chloro-1-[2-methyl-4-(2-methyl-benzoylamino)-benzoyl]-2,3,4,5-tetrahydro-1H-benzo[b]azepin-5-yl} iodomethyl carbonate as slightly yellow powder.

$^1$H-NMR (toluene-d$_8$, 100° C.) δppm:
1.3-1.8 (4H, m), 2.31 (3H, s), 2.42 (3H, s), 2.7-4.3 (2H, m), 5.48 (2H, d, J=5.1 Hz), 5.53 (2H, d, J=5.1 Hz), 5.5 (1H, m), 6.4-6.8 (3H, m), 6.8-7.2 (6H, m), 7.2 (1H, m), 7.36 (1H, s).

EXAMPLE 24

Acetoxymethyl {7-chloro-1-[2-methyl-4-(2-methyl-benzoylamino)-benzoyl]-2,3,4,5-tetrahydro-1H-benzo[b]azepin-5-yl} carbonate Sodium acetate (300 mg) was added to an acetonitrile solution (5 ml) of {7-chloro-1-[2-methyl-4-(2-methyl-benzoylamino)-benzoyl]-2,3,4,5-tetrahydro-1H-benzo[b] azepin-5-yl}iodomethyl carbonate, and then the mixture was heated under reflux for 8 hours. The reaction mixture was cooled to room temperature and the insoluble substance was removed by filtration. The filtrate was concentrated under reduced pressure and the residue was purified by silica gel flash chromatography (n-hexane:ethyl acetate=71:29→30:70). The purified product was concentrated under reduced pressure. The aqueous acetonitrile solution of the residue was freeze-dried to obtain 6.1 g of acetoxymethyl {7-chloro-1-[2-methyl-4-(2-methyl-benzoylamino)-benzoyl]-2,3,4,5-tetrahydro-1H-benzo[b]azepin-5-yl} carbonate as white amorphous solid.

$^1$H-NMR (Toluene-d$_8$, 100° C.) δppm: 1.3-1.8 (4H, m), 1.6 (3H, s), 2.3 (3H, s), 2.4 (3H, s), 2.7-4.4 (2H, m), 5.6 (2H, dd, J=5.5 Hz, 10.4 Hz), 5.6-5.9 (1H, m), 6.5 (1H, d, J=8.4 Hz), 6.6 (1H, br), 6.7 (1H, dd, J=2.3, 8.4 Hz), 6.8-7.2 (5H, m), 7.3 (1H, d, J=2.1 Hz), 7.4 (1H, 1.6 Hz)

EXAMPLE 25

7-Chloro-1-[2-methyl-4-(2-methyl-benzoylamino)-benzoyl]-5-methylthiomethoxy-2,3,4,5-tetrahydro-1H-benzo[b]azepine Dimethylsulfoxide (DMSO) (3 ml), acetic anhydride (1.5 ml), and acetic acid (1.5 ml) were added to tolvaptan (1.0 g, 2.2 mmol), and the mixture was stirred at 70° C. for 4 hours. Water and 1N aqueous sodium hydroxide solution were added to the reaction mixture, and the mixture was extracted with ethyl acetate, washed with an aqueous saturated sodium chloride solution, dried over anhydrous sodium sulfate. After filtration and concentration under reduced pressure, the residue was purified by silica gel flash chromatography (n-hexane:ethyl acetate=80:20→20:80). The purified product was concentrated under reduced pressure to obtain 0.62 g of 7-chloro-1-[2-methyl-4-(2-methyl-benzoylamino)-benzoyl]-5-methylthiomethoxy-2,3,4,5-tetrahydro-1H-benzo[b] azepine as white amorphous solid.

$^1$H-NMR (DMSO-d$_5$, 100° C.) δppm:
1.7-2.2 (4H, m), 2.17 (3H, s), 2.36 (6H, s), 2.6-4.3 (2H, m), 4.70 (2H, d, J=11.2 Hz), 4.83 (2H, d, J=11.2 Hz), 4.9 (1H, m), 6.7-7.0 (1H, m), 7.0-7.5 (8H, m), 7.56 (1H, s), 9.8 (1H, br).

EXAMPLE 26

{7-Chloro-1-[2-methyl-4-(2-methyl-benzoylamino)-benzoyl]-2,3,4,5-tetrahydro-1H-benzo[b]azepin-5-yloxymethyl} Dihydrogen Phosphate 7-Chloro-1-[2-methyl-4-(2-methyl-benzoylamino)-benzoyl]-5-methylthiomethoxy-2,3,4,5-tetrahydro-1H-benzo[b]azepine (509 mg, 1.0 mmol) was dissolved in 1, 2-dichloroethane (10 ml). Sulfuric chloride (0.12 ml, 1.5 mmol) was added thereto, and the mixture was stirred at room temperature for 15 minutes. The reaction mixture was concentrated under reduced pressure. Acetonitrile (10 ml), formic acid (0.68 ml, 10 mmol), and triethylamine (1.4 ml, 10 mmol) were added to the residue, and the mixture was stirred at 70° C. for 30 minutes. After cooling to room temperature, water was added thereto, and the mixture was extracted with ethyl acetate. The organic layer was extracted with an aqueous saturated sodium hydrogen carbonate solution twice. Citric acid was gradually added to the aqueous layer until no foam was observed, and the aqueous layer was extracted with dichloromethane twice. The combined organic layer was dried over anhydrous sodium sulfate. After filtration and concentration under reduced pressure, the residue was dissolved in ethyl acetate under heating, and the insoluble substance was removed by filtration while it is hot. After cooling the filtrate, the resulted precipitates were collected by filtration and dried to obtain 180 mg of {7-chloro-1-[2-methyl-4-(2-methyl-benzoylamino)-benzoyl]-2,3,4,5-tetrahydro-1H-benzo[b]azepin-5-yloxymethyl} dihydrogen phosphate as white powder.

$^1$H-NMR (DMSO-d$_6$, 100° C.) δppm:
1.6-2.2 (4H, m), 2.3-2.4 (6H, m), 2.8-4.3 (2H, m), 4.9-5.2 (2H, m), 5.2-5.3 (1H, m), 6.7-7.7 (10H, m), 9.81 (1H, br).

EXAMPLE 27

5-Acetoxymethoxy-7-chloro-1-[2-methyl-4-(2-methyl-benzoylamino)-benzoyl]-2,3,4,5-tetrahydro-1H-benzo[b]Azepine 7-Chloro-1-[2-methyl-4-(2-methyl-benzoylamino)-benzoyl]-5-methylthiomethoxy-2,3,4,5-tetrahydro-1H-benzo[b]azepine (509 mg, 1.0 mmol) was dissolved in 1,2-dichloroethane (10 ml). Sulfuric chloride (0.12 ml, 1.5 mmol) was added thereto, and the mixture was stirred at room temperature for 15 minutes. The obtained mixture was concentrated under reduced pressure, and acetonitrile (10 ml), sodium acetate (246 mg, 2.0 mmol), and sodium iodide (450 mg, 3.0 mmol) were added to the residue, and then the mixture was heated under reflux for 1 hour. After cooling to room temperature, ethyl acetate was added thereto, and the insoluble subject was removed by filtration. The filtrate was concentrated under reduced pressure, and the residue was purified by silica gel flash chromatography (n-hexane:ethyl acetate=65:35→50:50). The purified product was concentrated under reduced pressure, and the residue was dissolved in aqueous acetonitrile. After concentration at room temperature under reduced pressure, the resulted precipitates were collected by filtration, and dried to obtain 280 mg of 5-acetoxymethoxy-7-chloro-1-[2-methyl-4-(2-methyl-benzoylamino)-benzoyl]-2,3,4,5-tetrahydro-1H-benzo[b]azepine as white powder.

$^1$H-NMR (toluene-d$_8$, 100° C.) δppm:
1.3-1.9 (7H, m), 2.32 (3H, s), 2.41 (3H, s), 2.8-4.1 (2H, m), 4.6-4.8 (1H, m), 5.17 (2H, s), 6.4-6.8 (3H, m), 6.8-7.3 (6H, m), 7.39 (1H, s).

EXAMPLE 28

{7-Chloro-1-[2-methyl-4-(2-methyl-benzoylamino)-benzoyl]-2,3,4,5-tetrahydro-1H-benzo[b]azepin-5-yl} (2-chloroethyl)Carbamate Tolvaptan (1.0 g, 2.2 mmol) was suspended in toluene (7 ml). 2-Chloroethyl isocyanate (0.28 ml, 3.3 mmol) and 4-dimethylaminopyridine (DMAP) (27 mg, 0.22 mmol) were added thereto, and the mixture was stirred at 80° C. for 24 hours. After cooling to room temperature, the insoluble materials were filtered off and washed with ethyl acetate. The filtrate was concentrated under reduced pressure. The residue was purified by silica gel flash chromatography (n-hexane: ethyl acetate=54:46→33:67). The purified product was concentrated under reduced pressure to obtain 1.0 g of {7-chloro-1-[2-methyl-4-(2-methyl-benzoylamino)-benzoyl]-2,3,4,5-tetrahydro-1H-benzo[b]azepin-5-yl} (2-chloroethyl) carbamate as white amorphous solid.

$^1$H-NMR (DMSO-d$_6$, 100° C.) δppm:
1.6-2.2 (4H, m), 2.36 (6H, s), 2.6-4.3 (2H, m), 3.42 (2H, t, J=6.0 Hz), 3.64 (2H, dd, J=6.0, 12.1 Hz), 5.8-5.9 (3H, m), 6.7-7.5 (10H, m), 7.56 (1H, s), 9.8 (1H, br).

EXAMPLE 29

(2-{7-Chloro-1-[2-methyl-4-(2-methyl-benzoylamino)-benzoyl]-2,3,4,5-tetrahydro-1H-benzo[b]azepin-5-yloxycarbonylamino}-ethyl)-trimethyl-ammonium Chloride Trimethylamine (30% solution, 0.5 ml) was added to an ethanol solution (10 ml) of {7-chloro-1-[2-methyl-4-(2-methyl-benzoylamino)-benzoyl]-2,3,4,5-tetrahydro-1H-benzo[b]azepin-5-yl}(2-chloroethy)carbamate (330 mg), and the mixture was heated at 170° C. for 15 minutes (microwave reactor). After cooling to room temperature, the reaction mixture was concentrated under reduced pressure. To the residue was added ethyl acetate, and the resulted precipitates were collected by filtration and dried to obtain 120 mg of (2-{7-chloro-1-[2-methyl-4-(2-methyl-benzoylamino)-benzoyl]-2,3,4,5-tetrahydro-1H-benzo[b]azepin-5-yloxycarbonylamino}-ethyl)-trimethyl-ammonium chloride as white powder.

$^1$H-NMR (DMSO-d$_6$, 100° C.) δppm:
1.6-2.2 (4H, m), 2.34 (3H, s), 2.37 (3H, s), 2.8-4.3 (2H, m), 3.1-3.9 (9H, m), 3.3-3.7 (5H, m), 5.8-6.0 (1H, m), 6.7-7.1 (2H, m), 7.1-7.5 (7H, m), 7.56 (1H, s), 9.88 (1H, br).

EXAMPLE 30

{7-Chloro-1-[2-methyl-4-(2-methyl-benzoylamino)-benzoyl]-2,3,4,5-tetrahydro-1H-benzo[b]azepin-5-yl} 2,2-dimethyl-propionyloxymethyl Succinate Amorphous of {7-Chloro-1-[2-methyl-4-(2-methyl-benzoylamino)-benzoyl]-2,3,4,5-tetrahydro-1H-benzo[b]azepin-5-yl} 2,2-dimethyl-propionyloxymethyl succinate was prepared in a similar manner as in the above Example 5.

$^1$H-NMR (DMSO-d$_5$, 100° C.) δppm:
1.14 (9H, s), 1.75-2.10 (4H, m), 2.37 (6H, s), 2.65-2.80 (4H, m), 3.10-3.55 (1H, m), 3.65-4.15 (1H, m), 5.71 (2H, s), 5.85-6.00 (1H, m), 6.85-7.05 (2H, m), 7.10-7.25 (3H, m), 7.30-7.45 (4H, m), 7.55 (1H, s), 9.76 (1H, br).

EXAMPLE 31

{7-Chloro-1-[2-methyl-4-(2-methyl-benzoylamino)-benzoyl]-2,3,4,5-tetrahydro-1H-benzo[b]azepin-5-yl} (Ethoxycarbonylmethyl-methyl-carbamoyloxy) Acetate {7-Chloro-1-[2-methyl-4-(2-methyl-benzoylamino)-benzoyl]-2,3,4,5-tetrahydro-1H-benzo[b]azepin-5-yl} chloroacetate (500 mg, 0.95 mmol), ethyl sarcosinate hydrochloride (230 mg, 1.5 mmol), and potassium carbonate (414 mg, 3.0 mmol) were added to dimethylformamide (DMF) (5 ml), and the mixture was stirred at 60° C. for 1 hour. Water was added to the reaction mixture, and the resulted precipitates were collected by filtration and washed with water. The precipitates were dissolved in ethyl acetate, dried over anhydrous sodium sulfate, filtrated and concentrated under reduced pressure. The residue was purified by silica gel flash chromatography (n-hexane:ethyl acetate=36:64→15:85). The purified product was concentrated under reduced pressure. Water was added the residue, and resulted precipitates were collected by filtration and dried to obtain 330 mg of {7-chloro-1-[2-methyl-4-(2-methyl-benzoylamino)-benzoyl]-2,3,4,5-tetrahydro-1H-benzo[b]azepin-5-yl} (ethoxycarbonylmethyl-methyl-carbamoyloxy)acetate as white powder.

$^1$H-NMR (DMSO-$d_6$) δppm:
1.19 (3H, t, J=7.1 Hz), 1.6-2.2 (4H, m), 2.37 (6H, s), 2.8-4.3 (2H, m), 2.85 (2H, s), 2.96 (3H, s), 4.04 (2H, s), 4.13 (2H, q, J=7.1 Hz), 4.75 (2H, s), 5.9-6.1 (1H, m), 6.8-7.1 (2H, m), 7.1-7.3 (3H, m), 7.3-7.5 (4H, m), 7.56 (1H, s), 9.80 (1H, br).

EXAMPLE 32

{7-Chloro-1-[2-methyl-4-(2-methyl-benzoylamino)-benzoyl]-2,3,4,5-tetrahydro-1H-benzo[b]azepin-5-yl} [Methyl-(5-methyl-2-oxo-1,3-dioxol-4-yl-methoxycarbonyl)-amino]Acetate 7-Chloro-1-[2-methyl-4-(2-methyl-benzoylamino)benzoyl]-2,3,4,5-tetrahydro-1H-benzo[b]azepin-5-yl methylaminoacetate (0.34 g, 0.65 mmol), and (5-methyl-1,3-dioxolane-2-one-4-yl)-methyl 4-nitrophenyl carbonate (0.22 g, 0.74 mmol) were dissolved in DMF (5 ml), and the mixture was stirred at room temperature over night. Water was added to the reaction mixture, and the mixture was extracted with ethyl acetate. The organic layer was washed with water, an aqueous saturated sodium chloride solution, and then dried over sodium sulfate. After filtration and concentration, the residue was purified by silica gel chromatography (n-hexane:ethyl acetate) to obtain 0.44 g (43%) of {7-chloro-1-[2-methyl-4-(2-methyl-benzoylamino)-benzoyl]-2,3,4,5-tetrahydro-1H-benzo[b]azepin-5-yl} [methyl-(5-methyl-2-oxo-1,3-dioxol-4-yl-methoxycarbonyl)-amino]acetate as amorphous.

$^1$H-NMR (DMSO-$d_6$, 100° C.) δppm:
1.75-2.15 (4H, m), 2.10 (3H, s), 2.37 (6H, s), 2.96 (3H, s), 3.15-3.50 (1H, m), 3.70-4.25 (3H, m), 4.91 (2H, s), 5.95-6.05 (1H, m), 6.85-7.05 (2H, m), 7.10-7.45 (7H, m), 7.56 (1H, s), 9.76 (1H, br).

EXAMPLE 33

{7-Chloro-1-[2-methyl-4-(2-methyl-benzoylamino)-benzoyl]-2,3,4,5-tetrahydro-1H-benzo[b]azepin-5-yl} [Methyl-(5-methyl-2-oxo-1,3-dioxol-4-yl-methyl)-amino]Acetate Hydrochloride 4-Bromomethyl-5-methyl-1,3-dioxol-2-one (0.12 g, 0.61 mmol) was added to an acetonitrile (5 ml) solution of 7-chloro-1-[2-methyl-4-(2-methyl-benzoylamino)-benzoyl]-2,3,4,5-tetrahydro-1H-benzo[b]azepin-5-yl methylaminoacetate (0.30 g, 0.58 mmol) and triethylamine (0.10 ml, 0.69 mmol), and the mixture was stirred at room temperature over night. The reaction mixture was concentrated and water was added to the residue. The mixture was extracted with ethyl acetate, washed with an aqueous saturated sodium chloride solution, and dried over sodium sulfate. After filtration and concentration, the residue was purified by silica gel chromatography (n-hexane:ethyl acetate). The resulting residue was dissolved in ethyl acetate, and 4N hydrochloric acid-ethyl acetate was added thereto to form hydrochloride and then crystallized. The resulted crystals were collected by filtration and air-dried to obtain 90 mg (23%) of {7-chloro-1-[2-methyl-4-(2-methyl-benzoylamino)-benzoyl]-2,3,4,5-tetrahydro-1H-benzo[b]azepin-5-yl} [methyl-(5-methyl-2-oxo-1,3-dioxol-4-yl-methyl)-amino]acetate hydrochloride as white powder.

Melting point: 162.0-163.6° C.

$^1$H-NMR (DMSO-$d_6$, 100° C.) δppm:

1.75-2.15 (4H, m), 2.08 (3H, s), 2.37 (6H, s), 2.45-2.55 (3H, m), 3.15-4.10 (6H, m), 5.95-6.05 (1H, m), 6.85-7.05 (2H, m), 7.10-7.45 (7H, m), 7.56 (1H, s), 9.78 (1H, br).

EXAMPLE 34

{7-Chloro-1-[2-methyl-4-(2-methyl-benzoylamino)-benzoyl]-2,3,4,5-tetrahydro-1H-benzo[b]azepin-5-yl} [4-(2,2-dimethyl-propionyl)-piperazin-1-yl]Acetate Hydrochloride 1-{7-Chloro-1-[2-methyl-4-(2-methyl-benzoylamino)-benzoyl]-2,3,4,5-tetrahydro-1H-benzo[b]azepin-5-yloxycarbonylmethyl}-piperazine dihydrochloride (200 mg, 0.31 mmol) was dissolved in pyridine (2 ml). Trimethylacetylchloride (0.1 ml, 0.75 mmol) was added thereto, and the mixture was stirred at room temperature for 20 hours. Ethyl acetate was added to the reaction mixture, and the mixture was washed with a copper sulfate aqueous solution and a saturated sodium sulfate aqueous solution sequentially, dried over anhydrous sodium sulfate. After filtration and concentration under reduced pressure, the residue was purified by silica gel flash chromatography (ethyl acetate:methanol=100:0→98:2). The purified product was concentrated under reduced pressure, and a 4N hydrogen chloride ethyl acetate solution (0.5 ml) was added to the ethyl acetate solution (2 ml) of the residue. To the solution was added diethyl ether, and the resulted precipitates were collected by filtration and dried to obtain 70 mg of {7-chloro-1-[2-methyl-4-(2-methyl-benzoylamino)-benzoyl]-2,3,4,5-tetrahydro-1H-benzo[b]azepin-5-yl} [4-(2,2-dimethyl-propionyl)-piperazin-1-yl]acetate hydrochloride as white powder.

Melting point: 194-195° C.

$^1$H-NMR (DMSO-$d_6$) δppm:

1.20 (9H, s), 1.6-2.2 (4H, m), 2.33 (3H, s), 2.37 (3H, s), 2.7-3.0 (1H, m), 3.44 (8H, brs), 4.0-5.0 (3H, m), 6.0-6.2 (1H, m), 6.6-7.8 (10H, m), 10.29 (1H, s).

Table 1 shows chemical formulae of the compounds obtained in Examples 1 to 34.

TABLE 1

[Structure: core compound with 7-chloro-2,3,4,5-tetrahydro-1H-benzo[b]azepine bearing OR¹ at C5, N-linked to 2-methyl-4-(2-methylbenzamido)benzoyl group]

| Example | R¹ | Salt |
|---|---|---|
| 1 | —CO(CH₂)₂CO₂H | — |
| 2 | —CO(CH₂)₂CO₂⁻ Na⁺ | — |
| 3 | —CO(CH₂)₂CO₂⁻ K⁺ | — |
| 4 | —CO(CH₂)₃CO₂⁻ Na⁺ | — |
| 5 | —CO(CH₂)₂CO₂CH₃ | — |
| 6 | —CO(CH₂)₂CONH(CH₂)₂OH | — |
| 7 | —COCH₂SCH₂CO₂H | — |
| 8 | —COCH₂SCH₂CO₂CH₃ | — |
| 9 | —COCH₂S(O)₂CH₂CO₂CH₃ | — |
| 10 | —CO(CH₂)₁₄CH₃ | — |
| 11 | —COCH₂Cl | — |
| 12 | —COCH₂-N(piperazine)-N-CO-O-C(CH₃)₃ (Boc-piperazinyl acetyl) | — |
| 13 | —COCH₂-N(piperazine)-NH | 2HCl |
| 14 | —COCH₂-N(piperazine)-N-CH₃ | 2HCl |
| 15 | —CO(CH₂)₃N(CH₃)₂ | HCl |
| 16 | —CO(CH₂)₃Cl | — |
| 17 | —CO(CH₂)₃-N(piperazine)-N-COCH₃ | — |
| 18 | —COCH₂N(CH₃)CO₂CH(CH₃)Cl | — |
| 19 | —COCH₂N(CH₃)CO₂CH(CH₃)OCOCH₃ | — |
| 20 | —CO-C(CH₃)₂-CH₂-(2-OP(O)(OBn)₂-3,5-dimethylphenyl) (dibenzyl phosphate ester) | — |
| 21 | —CO-C(CH₃)₂-CH₂-(2-OP(O)(OH)₂-3,5-dimethylphenyl) (phosphate) | — |
| 22 | —CO₂CH₂Cl | — |
| 23 | —CO₂CH₂I | — |
| 24 | —CO₂CH₂OCOCH₃ | — |
| 25 | —CH₂SCH₃ | — |
| 26 | —CH₂OPO(OH)₂ | — |
| 27 | —CH₂OCOCH₃ | — |
| 28 | —CH₂CONH(CH₂)₂Cl | — |
| 29 | —CONH(CH₂)₂N⁺(CH₃)₃ Cl⁻ | — |
| 30 | —CO(CH₂)₂CO₂CH₂OCOC(CH₃)₃ | — |
| 31 | —COCH₂OCON(CH₃)CH₂CO₂CH₂CH₃ | — |
| 32 | —COCH₂N(CH₃)CO-O-CH₂-(4-methyl-2-oxo-1,3-dioxol-5-yl) | — |
| 33 | —COCH₂N(CH₃)CH₂-(4-methyl-2-oxo-1,3-dioxol-5-yl) | HCl |
| 34 | —COCH₂-N(piperazine)-N-CO-C(CH₃)₂-CH₃ | HCl |

EXAMPLE 35 to Example 104

The compounds of the following Examples 36, 37, and 63 were prepared in the same manner as the above Example 1, using corresponding starting materials.

The compounds of the following Examples 62, 64, 65, 66, 86, and 87 were prepared in the same manner as the above Example 5, using corresponding starting materials.

The compounds of the following Examples 35, 45, 46, 47, 48, 49, 50, 51, 52, 68, 92, 69, and 93 were prepared in the same manner as the above Example 10, using corresponding starting materials.

The compounds of the following Examples 42, 43, 67, 77, 78, 85, 95, and 103 were prepared in the same manner as the above Example 12, using corresponding starting materials.

The compounds of the following Examples 39, 55, 56, 57, 58, 60, 61, 74, 75, 76, 81, 82, and 84 were prepared in the same manner as the above Example 13, using corresponding starting materials.

The compounds of the following Examples 38, 41, 53, 54, 59, 70, 71, 72, 73, 79, 80, and 83 were prepared in the same manner as the above Example 15, using corresponding starting materials.

The compound of the following Example 91 was prepared in the same manner as the above Example 17, using corresponding starting materials.

The compounds of the following Examples 88, 89, and 90 were prepared in the same manner as the above Example 19, using corresponding starting materials.

The compound of the following Example 40 was prepared in the same manner as the above Example 24, using corresponding starting material.

The compound of the following Example 44 was prepared in the same manner as the above Example 28, using corresponding starting materials.

The compound of the following Example 94 was prepared in the same manner as the above Example 32, using corresponding starting materials.

The compounds of the following Examples 96, 97, 98, 99, 100, 101, 102, and 104 were prepared in the same manner as the above Example 34, using corresponding starting materials.

Table 2 shows chemical formulae and the physical properties, such as NMR and MS of the compounds obtained in Examples 35 to 104.

TABLE 2

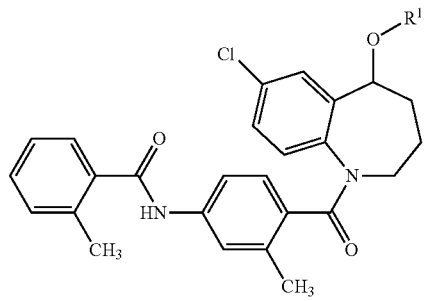

| Example | $R^1$ | NMR | MS | Salt |
|---|---|---|---|---|
| 35 | —CO(CH$_2$)$_4$CO$_2$CH$_3$ | 1H-NMR (DMSO-d6, 100° C.) δ ppm: 1.55-1.70 (4H, m), 1.75-2.05 (4H, m), 2.25-2.35 (2H, m), 2.37 (6H, s), 2.40-2.55 (2H, m), 3.15-3.50 (1H, m), 3.58 (3H, s), 3.75-4.15 (1H, m), 5.90-6.00 (1H, m), 6.85-7.05 (2H, m), 7.10-7.45 (7H, m), 7.56 (1H, s), 9.79 (1H, br). | 591 | — |
| 36 | —CO(CH$_2$)$_3$CO$_2$H | 1H-NMR (DMSO-d6) δ ppm: 1.7-2.1 (6H, m), 2.2-2.4 (8H, m), 2.5-2.55 (2H, m), 3.0-4.4 (2H, m), 5.9-6.0 (1H, m), 6.8-7.1 (2H, m), 7.1-7.3 (3H, m), 7.3-7.4 (4H, m), 7.57 (1H, s), 9.8 (1H, br). | 563 | — |
| 37 | —COCH$_2$OCH$_2$CO$_2$H | 1H-NMR (DMSO-d6) δ ppm: 2.2-2.6 (4H, m), 2.37 (6H, s), 3.0-4.4 (2H, m ), 4.13 (2H, s), 4.35 (2H, s), 5.9-6.1 (1H, m), 6.8-7.1 (2H, m), 7.1-7.3 (3H, m), 7.3-7.4 (4H, m), 7.57 (1H, s). 9.8 (1H, br). | 565 | — |
| 38 | —CO(CH$_2$)$_2$NHCO$_2$C(CH$_3$)$_3$ | 1H-NMR (DMSO-d6) δ ppm: 1.38 (9H, s), 1.6-2.2 (4H, m), 2.37 (6H, s), 2.5-2.7 (2H, m), 3.29 (2H, dd, J = 6.4 Hz, 12.9 Hz), 3.0-4.3 (2H, m), 5.8-6.1 (1H, m), 6.3 (1H, br), 6.8-7.1 (2H, m), 7.1-7.5 (7H, m), 7.56 (1H, s), 9.82 (1H, br). | 620 | — |
| 39 | —CO(CH$_2$)$_2$NH$_2$ | 1H-NMR (DMSO-d6) δ ppm: 1.6-2.2 (4H, m), 2.37 (3H, s), 2.38 (3H, s), 2.8-4.3 (2H, m), 2.9 (2H, t, J = 6.9 Hz), 3.1 (2H, t, J = 6.9 Hz), 5.9-6.1 (1H, m), 6.8-7.1 (2H, m), 7.1-7.3 (3H, m), 7.3-7.5 (4H, m), 7.56 (1H, s), 8.2 (3H, br), 9.87 (1H, br). | 520 | Hydrochloride |
| 40 | —CO$_2$CH$_2$OPO(OH)$_2$ | 1H-NMR (DMSO-d6) δ ppm: 1.3-2.1 (4H, m), 2.2-2.4 (6H, m), 2.0-4.0 (2H, m), 5.3-5.6 (2H, m), 5.7-6.0 (1H, m), 6.4-7.7 (10H, m), 10.0 (1H, br) | 603 | — |
| 41 | —CO(CH$_2$)$_2$CONH$_2$ | 1H-NMR (Toluene-d8) δ ppm: 1.5-1.8 (4H, m), 2.0-2.2 (2H, m), 2.31 (3H, s), 2.44 (3H, s), 2.4-2.6 (2H, m), 2.5-5.0 (2H, m), 4.0-4.7 (2H, m), 5.8-6.1 (1H, m), 6.4-6.8 (3H, m), 6.8-7.2 (5H, m), 7.29 (1H, s), 7.36 (1H, s). | 548 | — |
| 42 | —COCH$_2$NHCH$_2$CO$_2$CH$_3$ | 1H-NMR (DMSO-d6) δ ppm: 1.7-2.2 (4H, m), 2.38 (3H, s), 2.39 (3H, s), 2.8-4.3 (2H, m), 3.75 (3H, s), 3.85 (2H, s), 3.99 (2H, s), 6.0-6.2 (1H, m), 6.7-7.1 (2H, m), 7.1-7.3 (3H, m), 7.3-7.5 (4H, m), 7.56 (1H, s), 9.87 (1H, br). | 578 | Hydrochloride |
| 43 | —COCH$_2$N(CH$_3$)CH$_2$CO$_2$C$_2$H$_5$ | 1H-NMR (DMSO-d6) δ ppm: 1.21 (3H, t, J = 7.1 Hz), 1.7-2.2 (4H, m), 2.366 (3H, s), 2.371 (3H, s), 2.59 (3H, s), 2.8-4.3 (2H, m), 3.61 (2H, s), 3.77 (2H, s), 4.14 (2H, q, J = 7.1 Hz), 5.9-6.1 (1H, m), 6.8-7.1 (2H, m), 7.1-7.3 (3H, m), 7.3-7.5 (4H, m), 7.56 (1H, s), 9.80 (1H, br). | 606 | Hydrochloride |
| 44 | —CONHC$_2$H$_5$ | 1H-NMR (DMSO-d6) δ ppm: 1.09 (3H, t, J = 7.1 Hz), 1.6-2.2 (4H, m), 2.46 (6H, s), 2.85 (3H, s), 2.8-4.3 | 520 | — |

TABLE 2-continued

| | | (2H, m), 3.11 (2H, dq, J = 7.1, 5.7 Hz), 3.6-4.6 (1H, br), 5.7-5.9 (1H, m), 6.6-7.2 (4H, m), 7.2-7.5 (5H, m), 7.55 (1H, s), 9.79 (1H, br). | | |
|---|---|---|---|---|
| 45 | —CO(CH$_2$)$_8$CH$_3$ | 1H-NMR (CDCl3) δ ppm: 0.73-0.97 (3H, m), 1.11-2.59 (26.7H, m), 2.68-2.89 (1H, m), 2.98-3.97 (0.3H, m), 4.70-5.15 (1H, m), 5.85-6.17 (1.2H, m), 6.46-6.67 (1H, m), 6.84-7.68 (8.8H, m). | — | — |
| 46 | —CO(CH$_2$)$_{10}$CH$_3$ | 1H-NMR (CDCl3) δ ppm: 0.80-0.93 (3H, m), 1.13-2.62 (30.7H, m), 2.70-2.92 (1H, m), 2.99-3.95 (0.3H, m), 4.70-5.14 (1H, m), 5.84-6.16 (1.2H, m), 6.44-6.66 (1H, m), 6.85-7.78 (8.8H, m). | — | — |
| 47 | —CO(CH$_2$)$_{12}$CH$_3$ | 1H-NMR (CDCl3) δ ppm: 0.79-0.95 (3H, m), 1.10-2.63 (34.7H, m), 2.71-2.93 (1H, m), 2.98-4.03 (0.3H, m), 4.72-5.13 (1H, m), 5.88-6.16 (1.2H, m), 6.47-6.67 (1H, m), 6.86-7.74 (8.8H, m). | — | — |
| 48 | —CO(CH$_2$)$_{16}$CH$_3$ | 1H-NMR (CDCl3) δ ppm: 0.88 (3H, t, J = 6.6 Hz), 1.15-1.50 (28H, m), 1.60-1.95 (4H, m), 2.05-2.60 (9H, m), 2.75-2.95 (1H, m), 4.75-5.10 (1H, m), 5.85-6.10 (1H, m), 6.50-6.65 (1H, m), 6.85-7.05 (3H, m), 7.15-7.75 (8H, m). | 714 | — |
| 49 | —CO(CH$_2$)$_{18}$CH$_3$ | 1H-NMR (CDCl3) δ ppm: 0.88 (3H, t J = 6.7 Hz), 1.15-1.50 (32H, m), 1.60-2.00 (4H, m), 2.05-2.60 (9H, m), 2.75-2.95 (1H, m), 4.70-5.10 (1H, m), 5.85-6.10 (1H, m), 6.45-6.65 (1H, m), 6.85-7.10 (3H, m), 7.15-7.75 (8H, m). | 742 | — |
| 50 | —COC$_3$H$_7$ | 1H-NMR (CDCl3) δ ppm: 1.03 (3H, t, J = 7.3 Hz). 1.6-1.8 (4H, m), 2.0-2.5 (4H, m), 2.43 (3H, s), 2.45 (3H, s), 2.81 (1H, t, J = 11.6 Hz), 4.7-5.1 (1H, m), 5.9-6.1 (1H, m), 6.5-6.6 (1H, m), 6.9-7.9 (9H, m). | 519 | — |
| 51 | —CO(CH$_2$)$_4$CH$_3$ | 1H-NMR (CDCl3) δ ppm: 0.8-1.0 (3H, m), 1.2-1.4 (2H, m), 1.6-1.9 (4H, m), 2.1-2.6 (4H, m), 2.44 (3H, s), 2.46 (3H, s), 2.81 (1H, t, J = 11.5 Hz), 4.7-5.1 (1H, m), 5.8-6.1 (1H, m), 6.4-6.6 (1H, m), 6.9-7.7 (9H, m). | 547 | — |
| 52 | —CO(CH$_2$)$_6$CH$_3$ | 1H-NMR (CDCl3) δ ppm: 0.8-1.0 (3H, m), 1.2-1.5 (8H, m), 1.6-1.9 (4H, m), 2.0-2.5 (4H, m), 2.42 (3H, s), 2.44 (3H, s), 2.80 (1H, t, J = 11.5 Hz), 4.7-5.1 (1H, m), 5.9-6.1 (1H, m), 6.5-6.6 (1H, m), 6.9-8.0 (9H, m). | 575 | — |
| 53 | —COCH$_2$NHCOCH$_2$NHCO$_2$C(CH$_3$)$_3$ | 1H-NMR (CDCl3) δ ppm: 1.3-1.5 (9H, m), 1.7-1.9 (2H, m), 2.1-2.3 (2H, m), 2.4-2.6 (6H, m), 2.8-2.9 (1H, m), 3.6-4.3 (3H, m), 4.7-5.0 (1H, m), 5.1-5.3 (1H, m), 5.7-6.2 (2H, m), 6.5-8.0 (10H, m). | 663 | — |
| 54 | —COCH$_2$NHCOCH$_2$NHCOCH$_2$NHCO$_2$C(CH$_3$)$_3$ | 1H-NMR (CDCl3) δ ppm: 1.36 (9H, s), 1.7-2.0 (2H, m), 2.1-2.3 (2H, m), 2.4-2.6 (6H, m), 2.7-2.9 (1H, m), 3.8-4.4 (1H, m), 4.7-4.8 (1H, m), 4.9-5.3 (2H, m), 5.8-6.2 (2H, m), 6.5-8.2 (10H, m). | 720 | — |
| 55 | —COCH$_2$NHCOCH$_2$NH$_2$ | 1H-NMR (DMSO-d6) δ ppm: 1.6-2.2 (4H, m), 2.34 (3H, s), 2.36 (3H, s), 2.7-2.9 (1H, m), 3.6-3.8 (2H, m), 4.0-4.3 (2H, m), 4.6-4.8 (1H, m), 5.9-6.1 (1H, m), 6.6-7.8 (10H, m), 8.19 (3H, brs), 8.8-9.0 (1H, m), 10.27 (1H, s). | 563 | Hydro-chloride |
| 56 | —COCH$_2$NHCOCH$_2$NH$_2$ | 1H-NMR (DMSO-d6) δ ppm: 1.6-2.2 (4H, m), 2.34 (3H, s), 2.36 (3H, s), 2.6-3.0 (1H, m), 3.2-3.3 (2H, m), 3.9-4.2 (2H, m), 4.5-4.9 (1H, m), 5.7-6.1 (1H, m), 6.6-7.8 (10H, m), 8.0-8.4 (1H, m), 10.22 (1H, s). | 563 | — |
| 57 | —COCH$_2$NHCOCH$_2$NH$_2$ | 1H-NMR (DMSO-d6) δ ppm: 1.6-2.2 (4H, m), 2.34 (3H, s), 2.36 (3H, s), 2.8-3.0 (1H, m), 3.2-4.2 (4H, m), 4.5-4.9 (1H, m), 5.8-6.0 (1H, m), 6.47 (2H, s), 6.6-7.8 (10H, m), 8.5-8.7 (1H, m), 10.24 (1H, s). | 563 | Fumarate |
| 58 | —COCH$_2$NHCOCH$_2$NH$_2$ | 1H-NMR (DMSO-d6) δ ppm: 1.6-2.2 (4H, m), 2.30 (3H, s), 2.33 (3H, s), 2.36 (3H, s), 2.8-3.0 (1H, m), 3.4-3.8 (2H, m), 4.0-4.4 (2H, m), 4.6-4.9 (1H, m), 5.8-6.0 (1H, m), 6.6-7.8 (10H, m), 8.03 (3H, brs), 8.7-9.0 (1H, m), 10.25 (1H, s). | 563 | Methane-sulfonate |
| 59 | —COCH$_2$N(CH$_3$)CO$_2$C(CH$_3$)$_3$ | 1H-NMR (CDCl3) δ ppm: 1.3-1.5 (9H, m), 1.6-1.9 (2H, m), 2.0-2.3 (2H, m), 2.4-2.6 (6H, m), 2.7-3.0 (4H, m), 3.9-4.3 (2H, m), 4.7-5.1 (1H, m), 5.9-6.2 (1H, m), 6.5-6.7 (1H, m), 6.8-7.8 (10H, m). | 620 | — |
| 60 | —COCH$_2$NHCOCH$_2$NHCOCH$_2$NH$_2$ | 1H-NMR (DMSO-d6) δ ppm: 1.5-2.2 (4H, m), 2.34 (3H, s), 2.36 (3H, s), 2.8-3.0 (1H, m), 3.5-3.7 (1H, m), 3.8-4.2 (6H, m), 4.6-4.9 (1H, m), 5.8-6.1 (1H, m), 6.4-7.8 (10H, m), 8.11 (3H, brs), 8.5-8.9 (2H, m). | 620 | Hydro-chloride |
| 61 | —COCH$_2$NHCH$_3$ | 1H-NMR (DMSO-d6) δ ppm: 1.7-2.2 (4H, m), 2.33 (3H, s), 2.38 (3H, s), 2.64 (3H, s), 2.7-2.9 (1H, m), 4.0-4.4 (2H, m), 4.5-4.7 (1H, m), 6.0-6.2 (1H, m), 6.6-7.8 (10H, m), 9.40 (2H, brs), 10.29 (1H, s). | 520 | Hydro-chloride |

TABLE 2-continued

| | | | | |
|---|---|---|---|---|
| 62 | —CO(CH₂)₂CO₂C₂H₅ | 1H-NMR (DMSO-d6, 100° C.) δ ppm: 1.18 (3H, t, J = 7.1 Hz), 1.75-2.10 (4H, m), 2.37 (6H, s), 2.60-2.70 (2H, m), 2.70-2.80 (2H, m), 3.15-3.50 (1H, m), 3.75-4.10 (1H, m), 4.09 (2H, q, J = 7.1 Hz), 5.90-6.00 (1H, m), 6.85-7.05 (2H, m), 7.10-7.25 (3H, m), 7.30-7.45 (4H, m), 7.55 (1H, s), 9.76 (1H, br). | 577 | — |
| 63 | —CO(CH₂)₄CO₂H | 1H-NMR (DMSO-d6, 100° C.) δ ppm: 1.50-1.70 (4H, m), 1.75-2.10 (4H, m), 2.20-2.35 (2H, m), 2.37 (6H, s), 2.40-2.50 (2H, m), 3.15-3.50 (1H, m), 3.70-4.15 (1H, m), 5.90-6.00 (1H, m), 6.80-7.05 (2H, m), 7.10-7.25 (3H, m), 7.25-7.40 (4H, m), 7.56 (1H, s), 9.76 (1H, br), 11.30 (1H, br). | 577 | — |
| 64 | —CO(CH₂)₃CO₂CH₃ | 1H-NMR (DMSO-d6, 100° C.) δ ppm: 1.70-2.15 (6H, m), 2.35-2.45 (2H, m), 2.37 (6H, s), 2.50-2.60 (2H, m), 3.10-3.55 (1H, m), 3.60 (3H, s), 3.75-4.15 (1H, m), 5.90-6.00 (1H, m), 6.85-7.05 (2H, m), 7.10-7.25 (3H, m), 7.25-7.45 (4H, m), 7.56 (1H, s), 9.77 (1H, br). | 577 | — |
| 65 | —CO(CH₂)₂CO₂(CH₂)OH | 1H-NMR (DMSO-d6, 100° C.) δ ppm: 1.75-2.10 (4H, m), 2.37 (6H, s), 2.60-2.75 (4H, m), 3.10-3.50 (1H, m), 3.58 (2H, q, J = 5.4 Hz), 3.75-4.10 (1H, m), 4.08 (2H, t, J = 5.4 Hz), 4.24 (1H, t, J = 5.4 Hz), 5.90-6.00 (1H, m), 6.85-7.05 (2H, m), 7.10-7.45 (7H, m), 7.56 (1H, s), 9.76 (1H, br). | 593 | — |
| 66 | —CO(CH₂)₂CO₂CH₂CH(CH₃)₂ | 1H-NMR (DMS0-d6, 100° C.) δ ppm: 0.88 (6H, d, J = 6.7 Hz), 1.75-2.05 (5H, m), 2.37 (6H, s), 2.60-2.80 (4H, m), 3.15-3.55 (1H, m), 3.70-4.15 (1H, m), 3.85 (2H, d, J = 6.5 Hz), 5.90-6.00 (1H, m), 6.85-7.05 (2H, m), 7.10-7.25 (3H, m), 7.30-7.45 (4H, m), 7.55 (1H, s), 9.76 (1H, br). | 605 | — |
| 67 | —COCH₂N(CH₃)CH₂CO₂C₂H₅ | 1H-NMR (CDCl3) δ ppm: 1.02-1.34 (3H, m), 1.43-3.72 (23H, m), 3.75-4.28 (2H, m), 4.69-5.19 (1H, m), 5.85-6.16 (1.2H, m), 6.47-6.68 (1H, m), 7.86-8.04 (8.8H, m). | 633 | — |
| 68 | —COC(CH₃)₂OCOCH₃ | 1H-NMR (CDCl3) δ ppm: 1.40-2.63 (19.6H, m), 2.68-2.93 (1H, m), 3.02-4.03 (0.4H, m), 4.71-5.13 (1H, m), 5.88-6.15 (1.2H, m), 6.45-6.68 (1H, m), 6.82-7.78 (8.8H, m). | 576 | — |
| 69 | —COCH₃ | 1H-NMR (CDCl3) δ ppm: 1.63-1.96 (2H, m), 2.03-2.36 (2H, m), 2.25 (3H, s), 2.39-2.69 (6.6H, m), 2.72-2.95 (1H, m), 3.09-3.89 (0.4H, m), 4.70-5.16 (1H, m), 5.84-6.18 (1.2H, m), 6.48-6.67 (1H, m), 6.83-7.76 (8.8H, m). | — | — |
| 70 | —COCH₂NHCOCH₂N(CH₃)₂ | 1H-NMR (DMSO-d6) δ ppm: 1.6-2.2 (4H, m), 2.34 (3H, s), 2.37 (3H, s), 2.5-2.9 (6H, m), 3.9-4.1 (3H, m), 4.1-4.5 (2H, m), 4.5-4.9 (1H, m), 5.8-6.1 (1H, m), 6.6-8.0 (10H, m), 9.1-9.4 (1H, m), 10.11 (1H, brs), 10.28 (1H, s). | 591 | Hydro-chloride |
| 71 | —COCH₂NHCOCH₂N(CH₃)CO₂C(CH₃)₃ | 1H-NMR (CDCl3) δ ppm: 1.47 (9H, s), 1.7-1.9 (2H, m), 2.0-2.3 (2H, m), 2.44 (3H, s), 2.45 (3H, s), 2.7-3.0 (1H, m), 2.96 (3H, s), 3.8-4.4 (4H, m), 4.7-5.1 (1H, m), 5.9-6.2 (1H, m), 6.5-7.6 (10H, m), 7.71 (1H, brs). | 677 | — |
| 72 | —COCH₂N(CH₃)COCH₂NHCO₂C(CH₃)₃ | 1H-NMR (CDCl3) δ ppm: 1.44 (9H, s), 1.7-1.9 (2H, m), 2.0-2.3 (2H, m), 2.44 (3H, s), 2.46 (3H, s), 2.7-3.1 (1H, m), 3.11 (3H, s), 3.9-4.4 (4H, m), 4.7-5.1 (1H, m), 5.3-5.6 (1H, m), 5.8-6.2 (1H, m), 6.5-7.5 (10H, m), 7.68 (1H, brs). | 677 | — |
| 73 | —COCH₂N(CH₃)COCH₂N(CH₃)CO₂C(CH₃)₃ | 1H-NMR (CDCl3) δ ppm: 1.3-1.5 (9H, m), 1.5-1.9 (2H, m), 2.0-2.3 (2H, m), 2.44 (3H, s), 2.46 (3H, s), 2.7-3.1 (7H, m), 3.7-4.4 (4H, m), 4.7-5.1 (1H, m), 5.8-6.2 (1H, m), 6.4-6.6 (1H, m), 6.5-8.1 (10H, m). | 691 | — |
| 74 | —COCH₂NHCOCH₂NHCH₃ | 1H-NMR (DMSO-d6) δ ppm: 1.5-2.2 (4H, m), 2.34 (3H, s), 2.36 (3H, s), 2.56 (3H, s), 2.6-2.9 (1H, m), 3.7-3.9 (2H, m), 3.9-4.4 (2H, m), 4.5-4.9 (1H, m), 5.8-6.1 (1H, m), 6.6-7.8 (10H, m), 9.04 (2H, brs), 9.1-9.2 (1H, m), 10.28 (1H, s). | 577 | Hydro-chloride |
| 75 | —COCH₂N(CH₃)COCH₂NH₂ | 1H-NMR (DMSO-d6) δ ppm: 1.5-2.2 (4H, m), 2.34 (3H, s), 2.36 (3H, s), 2.6-3.0 (1H, m), 3.10 (3H, s), 3.6-4.1 (2H, m), 4.2-4.9 (3H, m), 5.8-6.1 (1H, m), 6.6-7.8 (10H, m), 8.27 (3H, brs), 10.29 (1H, s). | 577 | Hydro-chloride |
| 76 | —COCH₂N(CH₃)COCH₂NHCH₃ | 1H-NMR (DMSO0-d6) δ ppm: 1.5-2.2 (4H, m), 2.34 (3H, s), 2.36 (3H, s), 2.53 (3H, d, J = 4.1 Hz), 2.7-3.0 (1H, m), 3.09 (3H, s), 3.9-4.5 (4H, m), 4.6-5.0 (1H, m), 5.8-6.1 (1H, m), 6.6-7.8 (10H, m), 9.01 (2H, brs), 10.28 (1H, s). | 591 | Hydro-chloride |
| 77 | ![structure: CH₃-C(=O)-CH₂-N(morpholine)] | 1H-NMR (DMSO-d6) δ ppm: 1.6-2.2 (4H, m), 2.367 (3H, s), 2.374 (3H, s), 2.8-4.3 (2H, m), 2.7-3.0 (1H, m), 3.6-3.8 (4H, m), 4.3 (1H, br), 6.0-6.1 (1H, m), 6.8-7.1 (2H, m), 7.1-7.3 (3H, m), 7.3-7.5 (4H, m), 7.55 (1H, s), 9.8 (1H, br). | 576 | Hydro-chloride |

TABLE 2-continued

| | | | | |
|---|---|---|---|---|
| 78 | (structure) | 1H-NMR (DMSO-d6) δ ppm: 1.44 (3H, d, J = 7.1 Hz), 2.0-2.4 (4H, m), 2.37 (3H, s), 2.38 (3H, s), 2.8-4.3 (2H, m), 3.73 (3H, s), 3.9-4.0 (3H, m), 6.0-6.1 (1H, m), 6.8-7.1 (2H, m), 7.1-7.3 (3H, m), 7.3-7.5 (4H, m), 7.54 (1H, s), 9.86 (1H, br). | 592 | Hydrochloride |
| 79 | (structure) | 1H-NMR (CDCl3) δ ppm: 1.2-1.6 (12H, m), 1.7-2.0 (2H, m), 2.1-2.3 (2H, m), 2.4-2.6 (6H, m), 2.7-2.9 (1H, m), 3.8-4.4 (1H, m), 4.7-4.8 (1H, m), 4.9-5.3 (2H, m), 5.8-6.2 (2H, m), 6.5-8.2 (10H, m). | 677 | — |
| 80 | (structure) | 1H-NMR (CDCl3) δ ppm: 1.2-1.4 (9H, m), 1.7-1.9 (2H, m), 2.0-2.3 (2H, m), 2.5-2.6 (6H, m), 2.7-3.2 (3H, m), 3.7-4.5 (3H, m), 4.7-5.1 (1H, m), 5.8-6.1 (1H, m), 6.5-8.0 (15H, m). | 753 | — |
| 81 | (structure) | 1H-NMR (DMSO-d6) δ ppm: 1.3-1.5 (3H, m), 1.7-2.4 (4H, m), 2.34 (3H, s), 2.36 (3H, s), 2.7-2.9 (1H, m), 3.9 (1H, brs), 4.04.3 (2H, m), 4.5-4.9 (1H, m), 5.8-6.1 (1H, m), 6.6-7.8 (10H, m), 8.27 (3H, brs), 8.9-9.1 (1H, m), 10.26 (1H, s). | 577 | Hydrochloride |
| 82 | (structure) | 1H-NMR (DMSO-d6) δ ppm: 1.6-2.2 (4H, m), 2.32 (3H, s), 2.37 (3H, s), 2.7-3.2 (3H, m), 4.0-4.3 (3H, m), 4.5-4.9 (1H, m), 5.9-6.1 (1H, m), 6.6-7.7 (15H, m), 8.27 (3H, brs), 8.9-9.3 (1H, m), 10.26 (1H, s). | 653 | Hydrochloride |
| 83 | (structure) | 1H-NMR (CDCl3) δ ppm: 1.2-1.4 (9H, m), 1.6-2.2 (4H, m), 2.5-2.6 (6H, m), 2.7-3.2 (5H, m), 4.2-4.5 (1H, m), 4.7-5.1 (3H, m), 5.5-6.1 (1H, m), 6.4-8.1 (20H, m). | 843 | — |
| 84 | (structure) | 1H-NMR (DMSO-d6) δ ppm: 1.5-2.2 (4H, m), 2.3-2.4 (6H, m), 2.6-3.2 (5H, m), 4.0-4.2 (1H, m), 4.5-4.8 (2H, m), 5.7-6.1 (1H, m), 6.6-7.8 (20H, m), 8.2 (3H, brs), 9.0-9.5 (1H, m), 10.2-10.5 (1H, m). | 743 | Hydrochloride |
| 85 | (structure) | 1H-NMR (DMSO-d6, 100° C.) δ ppm: 1.10-2.10 (17H, m), 2.37 (6H, s), 2.60-2.80 (4H, m), 3.15-3.50 (1H, m), 3.75-4.20 (1H, m), 4.45-4.65 (1H, m), 5.90-6.00 (1H, m), 6.55-6.70 (1H, m), 6.85-7.05 (2H, m), 7.10-7.45 (7H, m), 7.55 (1H, s), 9.76 (1H, br). | 719 | — |

TABLE 2-continued

| | Structure | 1H-NMR | | |
|---|---|---|---|---|
| 86 | (structure) | 1H-NMR (DMSO-d6, 100° C.) δ ppm: 1.21 (3H, t, J = 7.1 Hz), 1.44 (3H, d, J = 5.4 Hz), 1.75-2.10 (4H, m), 2.37 (6H, s), 2.60-2.80 (4H, m), 3.15-3.50 (1H, m), 3.60-4.10 (1H, m), 4.13 (2H, q, J = 7.1 Hz), 5.90-6.00 (1H, m), 6.64 (1H, q, J = 5.4 Hz), 6.85-7.05 (2H, m), 7.10-7.45 (7H, m), 7.55 (1H, s), 9.75 (1H, br). | 665 | — |
| 87 | (structure) | 1H-NMR (DMSO-d6, 100° C.) δ ppm: 1.75-2.05 (4H, m), 2.11 (3H, s), 2.37 (6H, s), 2.65-2.85 (4H, m), 3.15-3.45 (1H, m), 3.75-4.05 (1H, m), 4.93 (2H, s), 5.90-6.00 (1H, m), 6.85-7.05 (2H, m), 7.10-7.25 (3H, m), 7.30-7.45 (4H, m), 7.55 (1H, s), 9.75 (1H, br). | 661 | — |
| 88 | (structure) | 1H-NMR (DMSO-d6, 100° C.) δ ppm: 1.06 (6H, d, J = 7.0 Hz), 1.35-1.45 (3H, m), 1.60-2.10 (4H, m), 2.37 (6H, s), 2.45-2.60 (1H, m), 2.95 (3H, s), 3.10-3.50 (1H, m), 3.75-4.15 (1H, m), 4.17 (2H, s), 5.95-6.05 (1H, m), 6.55-6.70 (1H, m), 6.85-7.05 (2H, m), 7.15-7.45 (7H, m), 7.56 (1H, s), 9.76 (1H, br). | 678 | — |
| 89 | (structure) | 1H-NMR (CDCl3) δ ppm: 1.40-2.65 (16H, m), 2.75-2.90 (1H, m), 3.80-4.25 (2H, m), 4.70-5.15 (1H, m), 5.20-5.40 (1H, m), 5.90-6.20 (1H, m), 6.50-8.05 (12H, m). | 636 | — |
| 90 | (structure) | 1H-NMR (CDCl3) δ ppm: 0.95-2.60 (20H, m), 2.75-2.90 (1H, m), 3.75-4.25 (2H, m), 4.70-5.15 (1H, m), 5.20-5.40 (1H, m), 5.90-6.15 (1H, m), 6.45-8.00 (12H, m). | 664 | — |
| 91 | (structure) | 1H-NMR (CDCl3) δ ppm: 1.33-1.52 (9H, m), 1.58-3.88 (26H, m), 4.70-5.12 (1H, m), 5.88-6.18 (1.2H, m), 6.57-6.65 (1H, m), 6.82-7.82 (8.8H, m). | — | — |
| 92 | (structure) | 1H-NMR (DMSO-d6) δ ppm: 1.8-2.1 (4H, m), 2.36 (3H, s), 2.37 (3H, s), 2.8-4.3 (2H, m), 6.2-6.3 (1H, m), 6.8-7.1 (2H, m), 7.1-7.5 (7H, m), 7.58 (1H, s), 7.93 (2H, d, J = 5.8 Hz), 8.82 (2H, d, J = 5.8 Hz), 9.82 (1H, br), | 554 | Hydro-chloride |
| 93 | (structure) | 1H-NMR (CDCl3) δ ppm: 1.77-2.00 (2H, m), 2.10-2.67 (6.6H, m), 2.78-3.00 (1H, m), 3.07-4.04 (3.4H, m), 4.75-5.24 (1H, m), 6.02-7.77 (12.6H, m), 7.97-8.24 (2.4H, m), | — | — |
| 94 | (structure) | 1H-NMR (DMSO-d6, 100° C.) δ ppm: 1.70-2.15 (4H, m), 2.11 (3H, s), 2.37 (6H, s), 2.95-3.50 (1H, m), 3.60-4.25 (1H, m), 3.95 (2H, d, J = 6.1 Hz), 4.89 (2H, s), 5.90-6.05 (1H, m), 6.85-7.05 (2H, m), 7.10-7.45 (8H, m), 7.55 (1H, s), 9.80 (1H, br). | 662 | — |

TABLE 2-continued

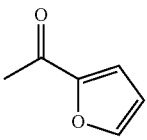

| Example | R¹⁰¹ | NMR | MS | Salt |
|---|---|---|---|---|
| 95 | —COCH₃ | 1H-NMR (DMSO-d6) δ ppm: 1.6-2.2 (7H, m), 2.37 (3H, s), 2.38 (3H, s), 2.8-4.3 (2H, m), 2.7-3.0 (4H, m), 3.4-3.7 (4H, m), 3.8 (2H, s), 5.3 (1H, br), 6.0-6.1 (1H, m), 6.8-7.1 (2H, m), 7.1-7.3 (3H, m), 7.3-7.5 (4H, m), 7.56 (1H, s), 9.8 (1H, br). | — | Hydrochloride |
| 96 | —COC₃H₇ | 1H-NMR (DMSO-d6) δ ppm: 0.90 (3H, t J = 7.4 Hz), 1.4-1.6 (2H, m), 1.8-2.2 (4H, m), 2.33 (3H, s), 2.38 (3H, s), 2.7-3.0 (1H, m), 3.40 (8H, brs), 3.8-5.0 (5H, m), 5.9-6.2 (1H, m), 6.6-7.8 (10H, m), 10.28 (1H, s). | 645 | Hydrochloride |
| 97 | —COC₆H₅ | 1H-NMR (DMSO-d6) δ ppm: 1.5-2.3 (4H, m), 2.33 (3H, s), 2.37 (3H, s), 2.6-2.8 (1H, m), 3.62 (8H, brs), 3.8-4.9 (3H, m), 5.9-6.2 (1H, m), 6.6-7.8 (15H, m), 10.28 (1H, s). | 679 | Hydrochloride |
| 98 | —CO(CH₂)₁₄CH₃ | 1H-NMR (DMSO-d6) δ ppm: 0.85 (3H, t J = 6.4 Hz), 1.23 (24H, brs), 1.48 (2H, brs), 1.7-2.2 (4H, m), 2.34 (3H, s), 2.38 (3H, s), 2.7-2.9 (1H, m), 3.40 (8H, brs), 3.6-5.0 (5H, m), 5.9-6.2 (1H, m), 6.6-7.8 (10H, m), 10.30 (1H, s). | 813 | Hydrochloride |
| 99 | —CO(CH₂)₂CO₂H | 1H-NMR (DMSO-d6) δ ppm: 1.6-1.9 (4H, m), 2.1-2.3 (2H, m), 2.4-2.9 (10H, m), 3.2-3.8 (9H, m), 4.7-5.1 (1H, m), 5.9-6.2 (2H, m), 6.5-6.7 (1H, m), 6.8-8.0 (10H, m). | 675 | Hydrochloride |
| 100 | —CO(CH₂)₂CO₂C₂H₅ | 1H-NMR (DMSO-d6) δ ppm: 1.17 (3H, t, J = 7.1 Hz), 1.6-2.2 (4H, m), 2.33 (3H, s), 2.38 (3H, s), 2.5-2.9 (4H, m), 3.39 (8H, brs), 4.0-5.0 (4H, m), 4.03 (2H, q, J = 7.1 Hz), 5.9-6.2 (1H, m), 6.6-7.8 (10H, m), 10.28 (1H, s), 10.8 (1H, brs). | 703 | Hydrochloride |
| 101 | —CO(CH₂)₃CO₂C₂H₅ | 1H-NMR (DMSO-d6) δ ppm: 1.18 (3H, t, J = 7.1 Hz), 1.6-2.3 (6H, m), 2.33 (3H, s), 2.38 (3H, s), 2.7-3.0 (4H, m), 3.42 (8H, brs), 4.0-4.9 (4H, m), 4.05 (2H, q, J = 7.1 Hz), 5.9-6.2 (1H, m), 6.6-7.8 (10H, m), 10.20 (1H, s), 11.0 (1H, brs). | 717 | Hydrochloride |
| 102 | —CO(CH₂)₂CO₂CH₃ | 1H-NMR (DMSO-d6) δ ppm : 1.6-2.2 (4H, m), 2.33 (3H, s), 2.38 (3H, s), 2.5-3.0 (4H, m), 3.36 (8H, brs), 3.56 (3H, s), 4.0-5.0 (4H, m), 5.9-6.2 (1H, m), 6.6-7.8 (10H, m), 10.27 (1H, s). | 689 | Hydrochloride |
| 103 | ![furan-2-yl ketone] | 1H-NMR (CDCl3) δ ppm: 1.67-1.93 (2H, m), 2.03-2.32 (2H, m), 2.38-2.94 (11H, m), 3.16-4.12 (7H, m), 4.75-5.14 (1H, m), 5.92-7.68 (14H, m). | 669 | — |
| 104 | —(CH₂)₂O(CH₂)₂OH | 1H-NMR (CDCl3) δ ppm: 1.02-1.34 (3H, m), 1.43-3.72 (23H, m), 3.75-4.28 (2H, m), 4.69-5.19 (1H, m), 5.85-6.16 (1.2H, m), 6.47-6.68 (1H, m), 7.86-8.04 (8.8H, m). | 633 | — |

TEST EXAMPLE 1

The compounds obtained in Examples 1, 50, and 52 were used as test compounds.

Each test compound, (Examples 1, 50, and 52) equivalent to 10 mg of tolvaptan, and hypromellose (125 mg) were suspended in 25 ml of water for injection in a porcelain mortar, to thereby obtain a suspension equivalent to 0.4 mg of tolvaptan per ml of suspension.

A spray-dried tolvaptan powder equivalent to 60 mg of tolvaptan, which was prepared in a similar manner to Example 3 of Japanese Unexamined Patent Publication No. 1999-21241, was suspended in 50 ml of water for injection in a porcelain mortar. This suspension was diluted three-fold with water for injection, preparing a suspension of spray-dried powder equivalent to 0.4 mg of tolvaptan per ml of suspension.

The following tests were conducted to examine the oral absorption features of each suspension. Male rats (body weight: about 180 g) that had been deprived of food for about 18 hours were used as test animals. The above suspensions were each administered by forced oral administration using a sonde for oral administration at a dose of 2.5 ml/kg of body weight, producing 1 mg of tolvaptan per kg of body weight. The blood samples were collected from the jugular vein under light diethyl ether anesthesia at the time of 0.5 hour, 1 hour, 2 hours, 4 hours, 6 hours, and 8 hours later after dosing. The serum concentrations of tolvaptan (ng/ml) were determined by using UPLC-MS/MS (Waters).

The average pharmacokinetic parameters were calculated from the results. The results are shown in the following table.

TABLE 3

| Test Compound | $AUC_\infty$ (ng·hr/mL) | $C_{max}$ (ng/mL) | $T_{max}$ (hr) | $MRT_\infty$ (hr) |
|---|---|---|---|---|
| Tolvaptan | 80.9 ± 28.5 | 26.4 ± 12.9 | 1.50 ± 0.58 | 2.95 ± 0.35 |
| Example 1 | 96.1 ± 18.1 | 16.2 ± 4.8 | 2.00 ± 0.00 | 4.45 ± 0.64 |
| Example 50 | 117.0 ± 26.1 | 21.6 ± 3.0 | 2.00 ± 0.00 | 4.78 ± 0.40 |
| Example 52 | 78.8 ± 41.7 | 11.6 ± 11.1 | 2.67 ± 1.15 | 9.10 ± 7.98 |

Mean ± S.D. (n = 3 or 4)

Table 3 reveals that, when administered in vivo, the test compounds indicate smaller Cmax than tolvaptan and the maximum drug concentration times ($T_{max}$) of the test compounds are delayed compared to tolvaptan. Consequently, the test compounds have prolonged effects.

TEST EXAMPLE 2

The compounds obtained in Examples 74 was used as test compounds.

The test compound, (Examples 1) equivalent to 10 mg of tolvaptan, and hydroxypropylcellulose (5 mg) was dissolved in 25 ml of water for injection in a porcelain mortar, to thereby obtain a solution equivalent to 0.4 mg of tolvaptan per ml.

A spray-dried tolvaptan powder equivalent to 10 mg of tolvaptan was suspended in 25 ml of water for injection in a porcelain mortar, to obtain a suspension of spray-dried powder equivalent to 0.4 mg of tolvaptan per ml of suspension.

The following tests were conducted to examine the oral absorption features of each suspension and solution. Male rats (body weight: about 160 g) that had been fasted for about 18 hours were used as test animals. The above suspension or solution were each administered by forced oral administration using a sonde for oral administration at a dose of 2.5 ml/kg of body weight, producing 1 mg of tolvaptan per kg of body weight. The blood samples were collected from the jugular vein under light diethyl ether anesthesia at the time of 0.5 hour, 1 hour, 2 hours, 3 hours, 4 hours, 6 hours, 8 hours and 10 hours later after dosing. The serum concentrations of tolvaptan (ng/ml) were determined by using UPLC-MS/MS (Waters).

The average pharmacokinetic parameters were calculated from the results. The results are shown in the following table.

TABLE 4

| Test Compound | $AUC_\infty$ (ng·hr/mL) | $C_{max}$ (ng/mL) | $T_{max}$ (hr) | $MRT_\infty$ (hr) |
|---|---|---|---|---|
| Tolvaptan | 92.4 ± 27.0 | 26.9 ± 11.6 | 1.00 ± 0.00 | 2.96 ± 0.47 |
| Example 74 | 79.0 ± 15.6 | 14.8 ± 6.4 | 4.00 ± 1.41 | 5.22 ± 0.51 |

Mean ± S.D. (n = 4)

Table 4 reveals that, when administered in vivo, the maximum drug concentration time ($T_{max}$) of the test compound is delayed compared to tolvaptan, and that the mean residence time (MRT) of the test compound is longer than that of tolvaptan. Consequently, the test compound has prolonged effect.

The invention claimed is:

1. A benzazepine compound represented by general formula (1)

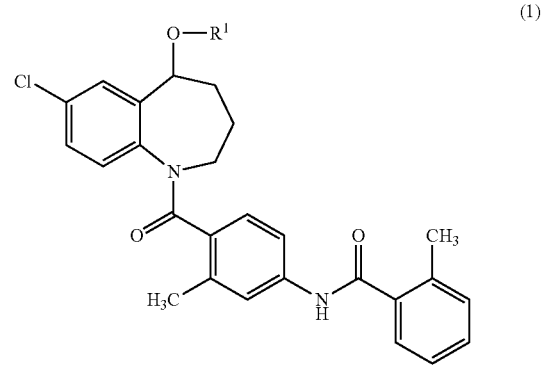

Wherein $R^1$ is a —CO—$R^8$ group (wherein $R^8$ is (8-1) an alkyl group optionally substituted with a halogen atom, a lower alkanoyloxy group, or a phenyl group substituted with a dihydroxy phosphoryloxy group in which the hydroxy groups are optionally substituted with benzyl groups, or a phenyl group substituted with a lower alkyl group and a dihydroxy phosphoryloxy group in which the hydroxy groups are optionally substituted with benzyl groups; (8-2) a lower alkoxy group substituted with a halogen atom, a lower alkanoyloxy group, or a dihydroxyphosphoryloxy group; (8-3) a pyridyl group; or (8-4) a lower alkoxyphenyl group.

2. The compound according to claim 1, wherein, in formula (1), $R^1$ is a —CO—$R^8$ wherein $R^8$ is an alkyl group, or a salt thereof.

3. A pharmaceutical preparation comprising the benzazepine compound of claim 1 or a pharmacologically acceptable salt thereof, and a pharmacologically acceptable diluent and/or carrier.

4. The pharmaceutical preparation according to claim 3 which is used as a vasodilator, hypotensive drug, aquaretic agent, or platelet aggregation inhibitor.

* * * * *